US005626629A

United States Patent [19]
Faltys et al.

[11] Patent Number: 5,626,629
[45] Date of Patent: May 6, 1997

[54] PROGRAMMING OF A SPEECH PROCESSOR FOR AN IMPLANTABLE COCHLEAR STIMULATOR

[75] Inventors: Michael A. Faltys, Northridge; James H. Wolfe, Canyon Country; Kitti McMeel, Simi Valley; Chris J. Hetlinger, Canyon Country, all of Calif.

[73] Assignee: Advanced Bionics Corporation, Sylmar, Calif.

[21] Appl. No.: 456,141

[22] Filed: May 31, 1995

[51] Int. Cl.$^6$ ..................................................... A61N 1/36
[52] U.S. Cl. ............................................................... 607/57
[58] Field of Search ................................. 607/55, 56, 57, 607/63, 64, 136, 137; 128/746; 381/68, 68.2, 68.4, 68.6

[56] References Cited

U.S. PATENT DOCUMENTS

| | | | |
|---|---|---|---|
| 4,232,679 | 11/1980 | Schulman . | |
| 4,400,590 | 8/1983 | Michelson | 179/107 |
| 4,424,812 | 1/1984 | Lesnick . | |
| 4,471,171 | 9/1984 | Köpke et al. | 179/107 R |
| 4,515,158 | 5/1985 | Patrick et al. | 607/57 |
| 4,532,930 | 8/1985 | Crosby et al. | 607/57 |
| 4,577,641 | 3/1986 | Hochmair et al. | 128/746 |
| 4,592,359 | 6/1986 | Galbraith . | |
| 4,612,934 | 9/1986 | Borkan | 607/57 |
| 4,617,913 | 10/1986 | Eddington | 607/57 |
| 4,677,679 | 6/1987 | Killion | 381/74 |
| 4,745,309 | 5/1988 | Waller | 307/490 |
| 4,901,353 | 2/1990 | Widin | 381/68.2 |
| 4,947,844 | 8/1990 | McDermott . | |
| 5,095,904 | 3/1992 | Seligman et al. | 607/57 |

FOREIGN PATENT DOCUMENTS

| | | | |
|---|---|---|---|
| 9501709 | 1/1995 | Australia | 381/68 |
| 0241101 | 10/1987 | European Pat. Off. . | |
| 0241101 | 10/1988 | European Pat. Off. . | |
| 3205685 | 8/1983 | Germany . | |
| 9208330 | 1/1991 | WIPO . | |

OTHER PUBLICATIONS

"A New Approach to the Cochlear Implant" by Ellis Douek et al, Jun. 1977, pp. 379–383, from Proc. roy. Soc. Med. vol. 70.

*Primary Examiner*—William E. Kamm
*Assistant Examiner*—George R. Evanisko
*Attorney, Agent, or Firm*—Fitch, Even, Tabin & Flannery

[57] ABSTRACT

A method and apparatus for fitting an auditory stimulation system involve, in one embodiment, coupling a programmer unit to an implanted unit implanted in the patient; prompting and/or assisting the operator to make and enter an objective or other measurement; receiving the objective measurements into the programmer unit; and determining an estimated threshold stimulation current for an electrode channel of the implanted unit as a function of the objective measurement. In another embodiment, the method and apparatus involve coupling a programmer unit to an implanted unit implanted in the patient; stimulating the patient with a speech signal; and displaying, in real time, a graphical representation of the speech signal using the programmer unit.

32 Claims, 15 Drawing Sheets

Patient Demographics

First Name:
Last Name:
Address:

City: State:
Postal Code/Zip:
Country:
Insurance Co:

Birthdate:
Patient ID:
Clinic Name:

Telephone Numbers
Home:
Work:
Insur. No.

Left Ear

Right Ear

Etiology
Progression
Surgeon
Surgery Date
Initial Fitting
Onset Age
Profound Deafness Age
Implant Serial #

Continue    Cancel    Help

PROGRAMMING OF A SPEECH PROCESSOR FOR AN IMPLANTABLE COCHLEAR STIMULATOR

BACKGROUND OF THE INVENTION

The present invention relates to programming of a speech processor for use with an implantable cochlear stimulator, and more particularly to a method and apparatus for fitting a speech processor and implantable cochlear stimulator by programming the speech processor. Even more particularly, the present invention relates to fitting the speech processor and implantable cochlear stimulator to a particular patient by programming the speech processor with a threshold stimulation level and a comfortable stimulation level, by programming an input dynamic range, and by programming a gain level.

Electrical stimulation of predetermined locations within the cochlea of the human ear through an intra-cochlear electrode array is described in U.S. Pat. No. 4,400,590. The electrode array shown comprises a plurality of exposed electrode pairs spaced along and imbedded in a resilient curved base for implantation in accordance with a method of surgical implantation described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 4,532,930 describes a multiple electrode stimulation system wherein only a single pulsatile output stimulates a single electrode channel at a given time. The single pulsatile output is generated on each of several electrodes in a sequential fashion, which unfortunately limits speed of operation and does not provide for analog operation wherein continuous stimulating signals of controllable amplitude are simultaneously applied to a number of electrode channels. Once a stimulator unit is implanted in a patient, there may only be limited means for monitoring ongoing circuit operation, e.g., selected parameters that are telemetered back to the external signal processor, or no means at all, in which case the circuit operation or power requirements of the unit cannot be monitored, or cannot be easily monitored, so as to optimize its continued operation.

U.S. Pat. No. 4,592,359 describes a cochlear implant system employing four current sources and four current sinks per channel. The four current sources and four current sinks are controlled by series switches to provide 16 indifferent circuits for applying 16 levels of two polarities to each output channel. In a pulsatile mode, the system provides for simultaneous update (amplitude control) and output to all channels. However, the system does not permit simultaneous analog update and output on all channels, and the electrode pairs for each channel are not electrically isolated from all other electrode pairs, creating the risk that undesired current leakage may occur. Once the stimulator is implanted, there is no means for monitoring its ongoing circuit operation or power requirements.

U.S. Pat. No. 4,947,844 shows a multiple channel electrode system, including an implanted receiver/stimulator connected to an implanted electrode array. The receiver/stimulator includes an electrode stimulating current control characterized in that current is delivered to each electrode or to each bipolar pair of electrodes in a series of short electrical pulses. Each elemental pulse is separated from the next by an interval of zero current, which has a longer duration than each elemental pulse. The waveform of the stimulus current comprises a series of pulses of one polarity followed by an equal number of pulses of another polarity whereby the sum of all electrical charge transferred through each electrode is approximately zero at the end of a stimulating current waveform. Simultaneous operation of the output channels is not possible and the number of channels cannot be greater than three or four without greatly reducing the duty cycle of the stimulating current waveform in each channel.

U.S. patent application Ser. No. 08/023,584, filed Feb. 26, 1993, of Schulman, et al., and incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array. (The ICS and SP disclosed in the referenced Schulman, et al. patent application is manufactuered and sold by the assignee of the present application under an exclusive license.)

The implantable cochlear stimulator is responsive to control signals from the speech processor and selectively monitors one or more of the electrodes, and voltages within the processor, in order to generate an implantable cochlear stimulator status indicating signal. The status indicating signal can be telemetered back to the speech processor, which, for example, may use the status indicating signal to control the power level of transmissions to the implantable cochlear stimulator.

The implantable cochlear stimulator described in the '065 application is also able to selectively control the pulse width of stimulating pulses that are applied through the electrode array to the cochlea, and the frequency at which the stimulating pulses are applied.

Thus, as the art of cochlear stimulation has advanced, both the implanted portion of the cochlear stimulation system, and the externally wearable processor (or speech processor) have become increasingly complicated and sophisticated. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor.

Unfortunately, currently available systems for programming (or fitting) of cochlear stimulation systems, while providing a degree of flexibility in the programming of the modes and methods of operation of the cochlear stimulation system, lack the ability to automate such procedures by establishing such modes and methods of operation based solely or in part of objective measurements taken from the patient.

The need for such a system becomes increasingly important as the ages of patients into which implantable cochlear stimulators are implanted decreases. This is because very young patients, for example, two year olds, are unable to provide adequate subjective feedback to the audiologist for the audiologist to accurately "fit" the cochlear stimulation system optimally for the patient. Furthermore, currently available programming units do not provide a level of feedback to the audiologist that enables the audiologist to independently evaluate the stimulation being applied to the patient, and thereby optimize such stimulation without guidance or with little guidance from the patient. Thus, what is needed is an improved apparatus and method for programming a speech processor of a cochlear stimulation system that provides for the utilization of objective measurements in the setting of the modes and methods of operation of the cochlear stimulation system, and further provides a mechanism of objective feedback to the audiologist so the audiologist can evaluate the stimulation being applied to the patient.

SUMMARY OF THE INVENTION

The present invention advantageously addresses the needs above as well as other needs by providing a system and method for fitting a speech processor and implantable cochlear stimulator to a particular patient by programming the speech processor.

In one embodiment, the invention can be characterized as a method of fitting an auditory stimulation system. The method includes the steps of coupling a programmer unit to an implanted unit implanted in the patient; prompting the operator to enter an objective measurement; receiving the objective measurement into the programmer unit; and determining an estimated threshold stimulation current for an electrode channel of the implanted unit as a function of the objective measurement. More specifically, the prompting may include prompting the operator to enter a stapedius reflex measurement, an electrically elicted acoustic reflex threshold (EART) measurement, or an electrically elicited auditory brainstem (EABR) response measurement.

In one variation the method also includes determining an estimated comfortable stimulation current for the electrode channel as a function of the objective measurement(s).

In order to further refine the estimated threshold stimulation current and the comfortable stimulation current, the method may include stimulating the patient through the implanted unit using the estimated threshold stimulation current on the electrode channel, and adjusting the estimated threshold stimulation current for the electrode channel in response to subjective feedback from the patient; and stimulating the patient through the implanted unit using the estimated comfortable stimulation current on the electrode channel, and adjusting the estimated comfortable stimulation current for the electrode channel in response to subjective feedback from the patient.

In another embodiment, the present invention may be characterized as method of fitting an auditory stimulation system having the following steps: coupling a programmer unit to an implanted unit implanted in the patient; stimulating the patient with a speech signal; and displaying, in real time, a graphical representation of the speech signal using the programmer unit. In one variation, the method includes mapping an estimated input dynamic range to an adjusted threshold stimulation current; and mapping a zero decibel gain to an adjusted comfortable stimulation current, the input dynamic range being measured relative to the zero decibel gain. The estimated input dynamic range and the zero decibel gain are displayed, in accordance with this variation, along with the graphical representation of the speech signal. Patient perception is adjusted via a graphic equalizor while watching the real-time speech signal on a screen display representation of VU meters. The graphic equalizer adjusts the gains of the speech signal on each channel before mapping. This allows certain frequency bands to be emphasized and/or de-emphasized.

The invention may also be characterized, in a further embodiment, as an apparatus having a programmer unit. The programmer unit prompts the operator to enter an objective measurement, receives the objective measurement, determines an estimated threshold stimulation current as a function of the objective measurement, and determines an estimated comfortable stimulation current as a function of the objective measurement. Then, the programmer unit optionally prompts the user so that such stimulation current may be further optimized subjectively by using live or standardized speech signals.

The apparatus may also include a clinician's programmer with a standard serial interface, coupled to the programmer unit, and a specialized serial interface including means for interfacing the clinician's programmer to the implantable cochlear stimulator. The clinician's programmer unit also has a protocol converter for converting a first protocol used by the standard serial interface to a second protocol used by the specialized serial interface.

In another further embodiment, the present invention can be characterized as an apparatus for fitting a patient with an implantable cochlear stimulator. This apparatus includes a programmer unit that causes the implantable cochlear stimulator to stimulate the patient with a speech signal, and then displays, in real time, a graphical representation of the speech signal using the programmer unit.

In a variation of the apparatus, an equalizer board is coupled to the programmer unit. The equalizer board includes a potentiometer for adjusting electrode channel gain on an electrode channel of the implantable cochlear stimulator, and a potentiometer for adjusting an input dynamic range. This allows the patient to peform their own subjective adjustment using live or standardized speech.

The system of the invention can also be used in conjunction with other instruments, such as an Evoked Potential or Impedance Bridge Machine. In such instance, the stimulation values may be entered on either a Stapedius or Evoked Potential Screen. When a "set level" command is entered, the value is accepted.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
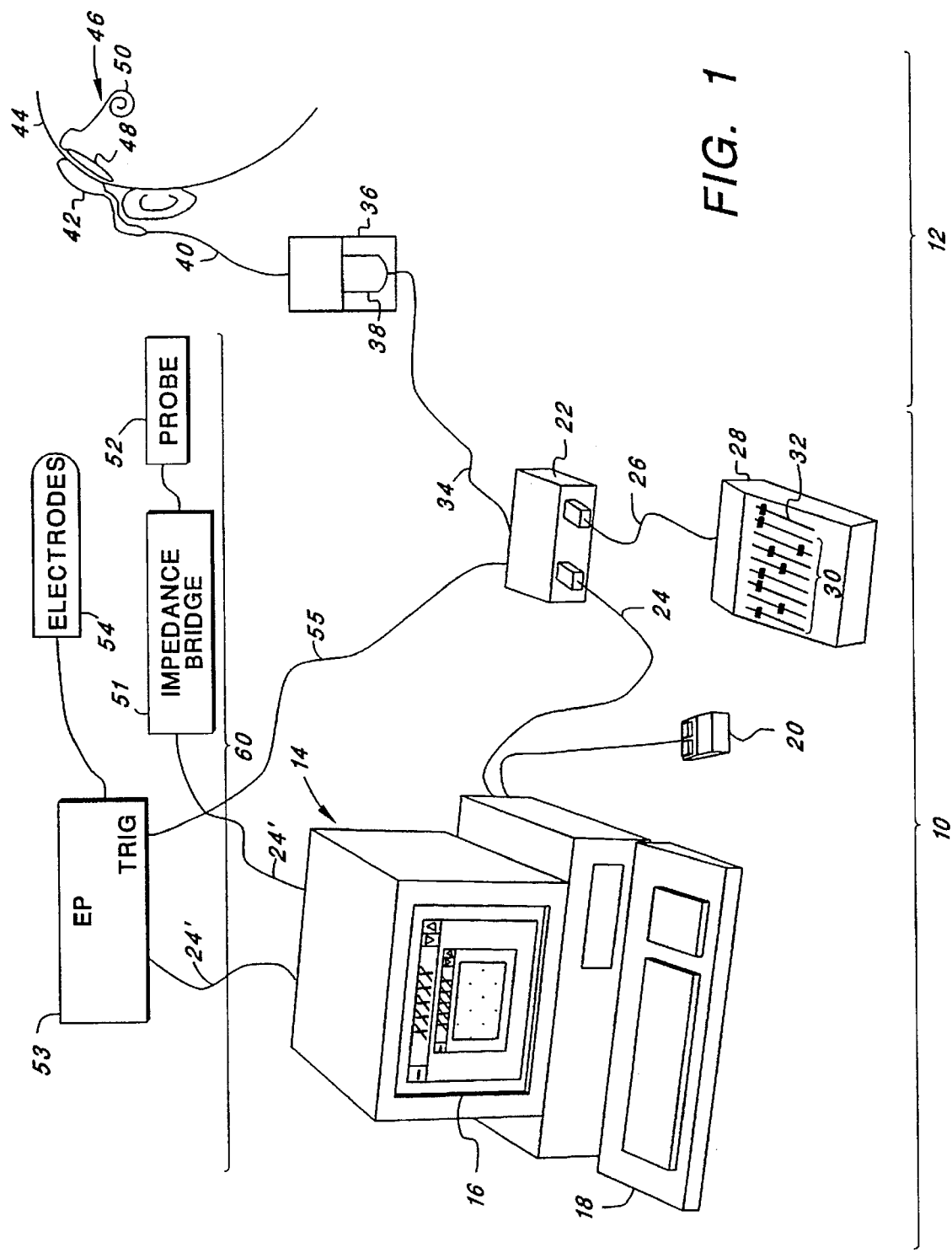
FIG. 1 is a schematic diagram illustrating components of a preferred embodiment of the present invention.

Referring first to FIG. 1, a schematic diagram is shown of components of a implantable cochlear stimulator (ICS) fitting system 10 coupled to a patient system 12. The ICS fitting system 10 employs a programmer unit 14, which is preferably a personal computer system such as an INTEL PENTIUM or 486 based personal computer running MICROSOFT WINDOWS, Version 3.1, or a compatiable windows program. The programmer unit includes a display screen, such as a super VGA-type cathode ray tube display, as an output device, and employs a keyboard 18 and a digitizing device 20, such as a mouse, as input devices. As the programmer unit 14, the display screen 16, the keyboard 18 and the digitizing device 20 are preferably of a type well known in the art, further description of these devices is not made herein except to the extent they have been customized or modified in order to carry out the teachings of the present embodiment. Coupled to the programmer unit 14 is a clinician's programmer 22. The coupling between the programmer unit 14 and the clinician's programmer 22 is achieved via, e.g., a serial interface, e.g., an RS 232 interface, such as is known in the art. A cable 24 is used to carry serial binary information between the clinician's programmer 22 and the programmer unit 14. Coupled to the clinician's programmer 22 via another cable 26 is a graphic equalizer board 28. The graphic equalizer board 28 consists of eight slider-type potentiometers 30, corresponding to eight stimulation channels of the patient system 12. A ninth slider-type potentiometer 32 is used to adjust an input dynamic range in the patient system 12. Operation of the graphic equalizer board 28 in accordance with the present embodiment is described in further detail below with reference to FIGS. 3A and 3B.

The ICS fitting system 10 is coupled to the patient system 12 through the clinician's programmer 22 via a cable 34. The cable 34 is coupled to a speech processor 36 of the patient system 12 via a connector 38. The connector 38 may, for example, be a DB25-type connector, such as is known in the art. It is via the cable 34 and connector 38 that serial binary information, which serial binary information is used to program the patient system 12 by the ICS fitting system 10, is transmitted and received. The transmission and reception of the serial binary interaction (or programming) between the clinician's programmer 22 and the speech processor 36 may be through a proprietary serial interface such as is implemented in the speech processor 36 using a commercially-available processor chip, e.g., Model No. 87C51 from INTEL. Within the clinician's programmer 22, information transmitted from the programmer unit 14 is converted to a proprietary serial protocol for transmission over the proprietary serial interface. Further description of the clinician's programmer 22 is made below in reference to FIG. 4.

The speech processor 36 is coupled via a connecting cable 40 to a supercutaneous transmitter/receiver coil 42. The coil 42 is placed against the skin 44 of a patient within whom an implanted cochlear stimulator (ICS) 46 has been implanted. The transmitter/receiver coil 42 is typically placed at a site near the patient's ear. The implantable cochlear stimulator 46 includes a subcutaneous transmitter/receiver coil 48 and an electrode array 50. The subcutaneous transmitter/receiver coil 48 is located below the patient's skin at the site where the supercutaneous transmitter/receiver coil 48 is to be placed. A suitable patient system 12 for use with the present embodiment is shown in the previously referenced U.S. patent Ser. No. 08/023,584 of Schulman, et al, copending herewith, and incorporated herein by reference.

Still referring to FIG. 1, objective audiological instrumentation 60 may optionally be coupled with the fitting system 10. Such instrumentation is known in the art, and typically includes an impedance bridge 51 coupled to a probe 52 that is inserted in the ear in conventional manner. An audiological evoked potential (EP) intrument 53 receives a trigger signal from the clinician's programmer 22 via cable 55. The EP instrument 53 receives signals from a set of electrodes 54 fitted on or in the ear in conventional manner. Both the EP instrument 53 and the impedance bridge 51 are further coupled to the programmer unit 14 via suitable cabling 24'. The use and operation of the audiological instrumentation 60 is conventional, although its use in combination with the fitting system 14 is new.

Figure 2:
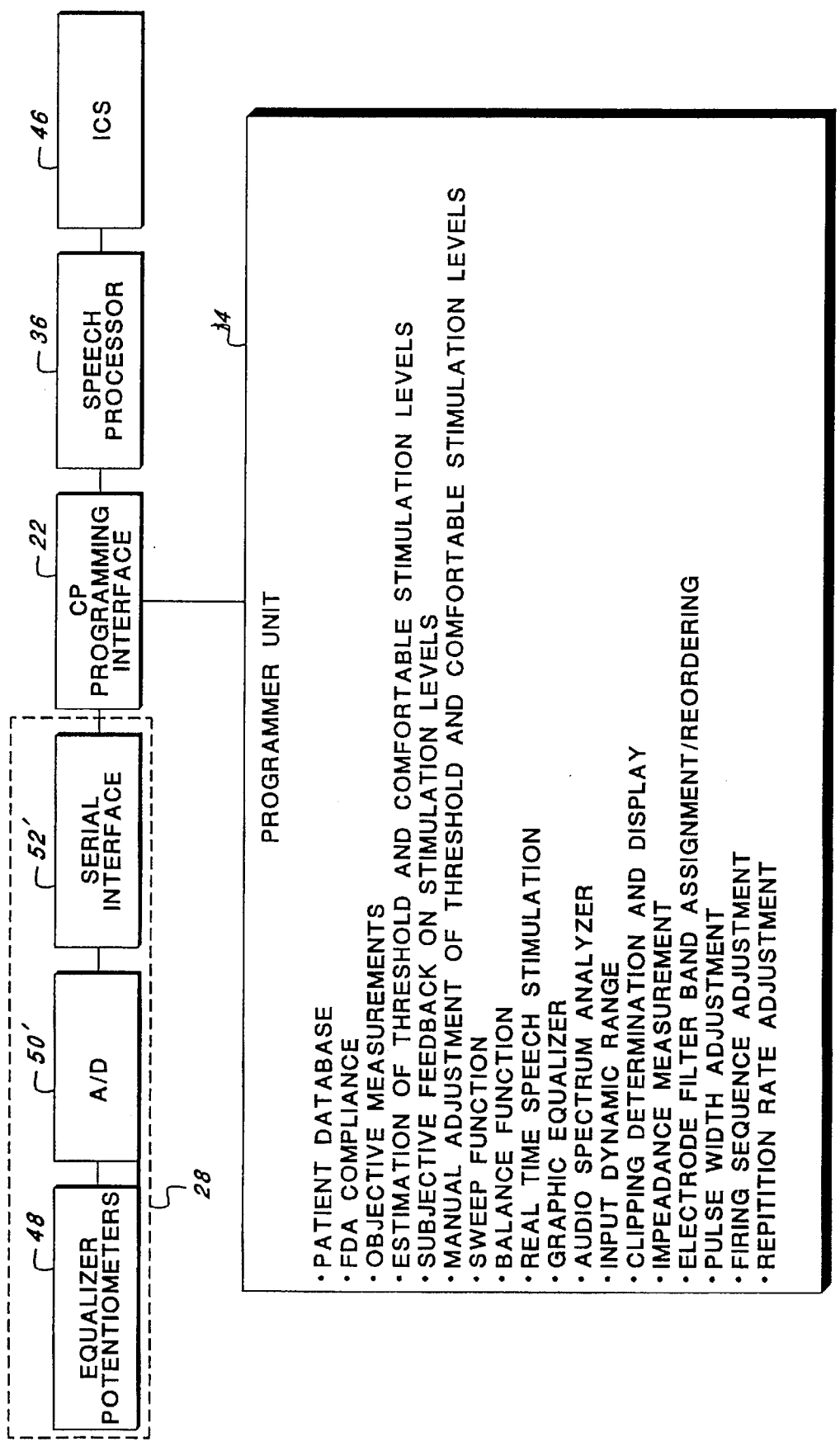
FIG. 2 is a block diagram showing functional elements of the preferred embodiment of FIG. 1.

Referring next to FIG. 2, a block diagram is shown of functional elements of the preferred embodiment. The graphic equalizer board 28 (which employs the nine slider-type potentiometers 30, 32) is shown in FIG. 2 as equalizer potentiometers 58, coupled through an analog-to-digital converter (A/D) 50' and a serial interface 52' to the clinician's programmer 22 (referred to in FIG. 2 as the CP programming interface). The clinician's programmer 22 is coupled to the speech processor 36, which in turn is coupled to the implantable cochlear stimulator 46; and to the programmer unit 14.

The programmer unit 14, which may be a personal computer, is modified with custom programming, described in more detail below with reference to FIGS. 3A and 3B, to carry out various functions of the present embodiment. These functions include maintenance of a patient database including demographic information and program information. The demographic information identifies the patients having implantable cochlear stimulators that are fitted with the ICS fitting system 10 of FIG. 1. The program information contains libraries of programs developed during fitting sessions that can be selectively downloaded into the speech processor 36, or used as a basis for generating new programs for the patient. The programmer unit 14 also is programmed to assure that various governmental regulations are complied with in the fitting of the patient system 12 in FIG. 1. For example, current regulations promulgated by the Food and Drug Administration (FDA) require the recordation of information regarding the particular fitting session, i.e., the threshold and most comfortable stimulation levels, and information regarding reasons for deactivating or shutting off one or more channels of the patient system 12. Advantageously, compliance with these and other regulatory requirements can be assured by including appropriate safeguards within the programs used to modify the programmer unit.

Another important aspect of the programmer unit 14 is the ability to record objective measurements taken from the patient either interoperatively or postoperatively. For example, one common objective measurement of value in the fitting of the implantable cochlear stimulator 46 is a stapedius reflex measure. Stapedius reflex is measured interoperatively by gradually increasing stimulation current applied through at least one channel of the electrode array 50 (FIG. 1) until contraction of the stapedius reflex muscle is observed in response to stimulation from the implantable cochlear stimulator 46 (or implant). Postoperatively, stapedius reflex is measured using a readily available audiological testing apparatus known as an audiological impedance bridge 51. In order to determine stapedius reflex postoperatively, the audiological impedance bridge is set to reflex decay mode to observe changes in middle ear compliance due to stimulations measured with probe 52 in the ipsi-on contralateral ear. As with the interoperative measurement of stapedius reflex, stimulation current is gradually increased until muscle contraction (through middle ear compliance) is detected by the audiological impedance bridge in response to stimulation from the implant 46.

Another objective measurement useful in the fitting of the patient system is the EABR. The EABR refers to the electrically elicited auditory brainstem response detected in response to stimulation through the electrode array 50 by the implant 46. The EABR is measured through electrodes 54 placed on the patient's earlobes and on top of the patient's head using an audiological EABR instrument 53, such as is known in the art. In order to measure the EABR, stimulation delivered through the electrode array 50 is gradually increased until an objective threshold of stimulation is observed through the audiological EABR instrument, which measures scalp potentials correlated with stimulation levels in the time domain. The audiological EABR instrument is preferably coupled to the programmer unit 14 through a serial interface in order to facilitate time domain correlations between the stimulation delivered and the scalp potentials measured. Stimulation and measurments generally must be repeated 50–100 times to separate the desired signal from noise. The programmer unit 14 advantageously supports such a protocol.

Based on the objective measurements entered through the keyboard 18 of the programmer unit 14, the programmer unit 14, under software control, estimates and displays a threshold stimulation level for each of the channels of the patient system 12, of which there are preferably eight. Such estimation can be determined by subtracting a fixed amount, in decibels, from the determined stapedius reflex stimulation level, or the determined EABR stimulation level. By way of example, 10 dB can be subtracted from these objective measurements in order to determine a threshold stimulation level. (The clinician's programmer 22 automatically makes the necessary adjustments, if any, to convert the units of measurement of the stapedius reflex stiulation level to the same units as the evoked potential stimulation level.) By measuring the stapedius reflex and/or EABR in response to stimulation pulses on each of the channels of the implantable stimulator, an estimated threshold stimulation level for each of the channels can be computed. Similarly, a maximum comfortable stimulation level for each of the channels can be estimated, for example, by subtracting an amount, in decibels, from the measured stapedius reflex. For example, by subtracting 6 dB from the determined stapedius reflex value, the estimated maximum comfortable stimulation level for each of the channels can be determined.

Advantageously, by determining estimated threshold and maximum comfortable stimulation levels for one or more of the channels of the patient system 12 based on objective measurements, the present invention facilitates use of the implantable cochlear stimulator with patients, such as children, who are otherwise unable to give reliable subjective feedback to an audiologist regarding the level of auditory stimulation experienced. Small children, of age two or less, can now be accurately fitted with an implantable cochlear stimulator 46 without the need for the child to accurately represent to the audiologist the amount of stimulation experienced. Advantageously, by implanting the implantable cochlear stimulator 46 on the patient at a young age, the chances of a fully functional hearing capability being achieved are great.

When the patient is able to provide subjective feedback to the audiologist regarding the stimulation levels experienced, the audiologist may make manual adjustment of the threshold and maximum comfortable, stimulation levels by moving graphical indicators on the display screen 16 of the programmer unit 14. Advantageously, independent graphical indicators are displayed for each of the channels of the patient system 12, so that the audiologist is able to adjust each of the threshold and maximum comfortable stimulation levels using a single screen display.

A sweep function is provided by the programmer unit 14 that causes sequential stimulation of each of the electrode channels in the electrode array 50. Ideally, the patient should experience stimulations corresponding to sounds that sweep from high pitched tones to low pitched tones, or vice versa, in response to the sweep function. If, however, the patient experiences tones that are not sequential, i.e., sound like they are out of tonal order, the audiologist can easily adjust the frequency bands of each of the stimulation channels in order to reorder the frequency bands so that the patient hears a sequence of tones that either increases in pitch or decreases in pitch. Such sweep functionality is important because the actual physiological order of the electrodes may in fact be altered during implantation if, for example, the tip of the electrode array is folded over within the cochlea during implantation. Advantageously, because the present embodiment provides for the non-invasive reordering of the electrode's channel frequency bands, problems such as electrode array foldover can be remedied noninvasively, i.e., without surgery.

Another function provided through the programming that modifies the programmer unit 14 is a balance function. The balance function allows for alternating stimulation of electrodes associated with pairs of, by default tonically adjacent, channels of the patient system 12. In response to such stimulation, the patient is able to subjectively evaluate the relative stimulation levels achieved by any two channels. If one of the two channels is subjectively "louder" sounding than the other, the audiologist is able to balance the stimulation provided by the two channels by adjusting up or down the maximum comfortable stimulation level for one of the two channels. Typically, the audiologist will ask the patient to compare the stimulation on adjacent channels, and then will make an adjustment to one of the channels until the channels balance in stimulation. Then, the audiologist will ask the patient to subjectively evaluate the stimulation provided by each of a next pair of channels. One of the channels in the next pair of channels is typically one of the two channels initially compared, and the other is a channel that has not yet been evaluated. The audiologist continues asking the patient to compare the stimulations on pairs of channels until each of the channels of the patient system 12 has been compared with each of its adjacent channels. (As used herein, the phrase "adjacent electrodes" or "adjacent channels" refers to electrodes or channels that are adjacent within the sound spectrum "heard" by the patient, i.e., tonically adjacent. Thus, "adjacent electrodes" are not necessarily physically adjacent, however, as a general rule, "adjacent electrodes" will be physically adjacent.)

A further function provided through the programming that modifies the programmer unit is real time speech stimulation. Real time speech stimulation, in addition to estimation of the threshold and maximum comfortable stimulation levels based on objective measurements, constitutes one of the significant enhancements provided in the present embodiment over presently available systems. When the real time speech stimulation function is activated, several components are displayed on the display screen, which have heretofore not been viewable in real time by the audiologist during a fitting session. One of the components is an audio spectrum analyzer, which constitutes a graphical representation of the relative stimulation level applied to each of the eight audio channels in response to sounds in its frequency band. Thus, for the first time, the audiologist is able to actually "see", in real time, what the patient is "hearing". The maximum comfortable stimulation levels for each of the channels are mapped to a 0 dB point on the audio spectrum analyzer, and the threshold stimulation levels are mapped to some lower point dependent upon the input dynamic range selected. The input dynamic range selected determines the range of sound amplitudes that will result in stimulation currents being generated at levels between the threshold stimulation level and the maximum comfortable stimulation level on the electrode array. By increasing the input dynamic range, i.e., moving the input dynamic range toward 0 dB, the level of background sounds "heard" by the patient is decreased because the level of sound needed before stimulation current at the threshold stimulation level is applied is greater. Similarly, by decreasing the input dynamic range, i.e., moving the input dynamic range down, away from the 0 dB point, the level of background heard by the patient is increased because the level of sound needed before the threshold stimulation level is applied is less.

A further feature of the real time speech stimulation function is the provision of a graphic equalizer on the display screen 16 through which the audiologist can adjust the gains applied to each of the channels of the implantable cochlear stimulator. Several equalizer "tools" are provided on the screen display to facilitate adjustment of the graphic equalizer by the audiologist. Advantageously, the graphic equalizer board 28, which is preferably operated by the patient during a fitting session, includes slider-type potentiometers 30 corresponding to each of eight channels of the implantable cochlear stimulator, which allow adjustment of the gains on each of these channels by the patient during a fitting session. The ninth slider-type potentiometer 32 can be operated by the patient in order to adjust the input dynamic range. In this way, the patient, in real time, is able to perform equalization adjustments and input dynamic range adjustment, of the sounds "heard" during a fitting session. Once the patient has adjusted the individual channel gains and the input dynamic range, on the graphic equalizer board, the audiologist can store the equalization scheme and input dynamic range into the speech processor 36 as part of a program for future use by the patient.

Another feature of the real time speech stimulation function is the display of "clipping" on the audio spectrum analyzer. Such "clipping" is represented graphically by changing the color of the bars in the audio spectrum analyzer once they exceed the 0 dB point (or line). For example, the bars may be green past the 0 dB line and may be red when sound levels exceed the patient's upper limit of sitmulation. The patient is not stimulated beyond this limit, the audiologist is simply shown that these limits could be exceeded. When clipping does occur, the audiologist is thus informed of this phenomenon by the change in color in the audio spectrum analyzer, so that the audiologist is able to independently determine when distortion of input sounds may be occurring. Such clipping can be minimized through careful adjustment of the graphic equalizer.

A further function of the programmer unit 14 is the ability to display audiological impedances as measured by the audiological instrumentation 60. When used, the impedance bridge 55 is triggered by the physician's programmer 22 through the cable 55 to alert the instrumentation 60 when stimulation is occurring. This allows correlation of the stimulus and measurement to reduce noise levels, and in general improves the overall efficiency of the fitting process.

As mentioned above, filter band assignments for each of the channels can be adjusted by the programmer unit 14. Such adjustment of the filter bands not only allows the audiologist to customize the frequency ranges (or bands) that will cause stimulation current to be applied to each of the electrodes, respectfully, but allows the audiologist to reorder the electrodes tonically so as to compensate for conditions such as foldover of the electrode array, which can occur during implantation.

Adjustment of the pulse widths used for stimulation in a continuous interleaved sampler strategy can also be made, as can adjustment of the firing sequence and repetition rate. The firing sequence is generally selected to be from high to low, i.e., beginning with electrodes near the opening or base of the cochlea and finishing with electrodes that are farthest inside the cochlea, i.e., at the apex of the cochlea, but may be selected to be from high to low or to be nonsequential. As described in U.S. patent application Ser. No. 08/322,065, the electrodes are sequentially (or nonsequentially) stimulated with pulses of electrical current during operation. The pulse width adjustment function of the programmer unit allows customization of the pulse width of the stimulation pulses applied to the electrodes during operation of the implantable cochlear stimulator 46. In accordance with some stimulation strategies, after a first electrode delivers its pulse having a selected pulse width and having a current amplitude commensurate with the level of stimulation to be delivered for its frequency band, a next electrode in the electrode array delivers a stimulation pulse having a selected pulse width and having a current amplitude commensurate with the level of stimulation to be delivered for its frequency band. An amount of time elapses between stimulation by the first electrode and stimulation by the next electrode in accordance with the repetition rate adjustment. The repetition rate adjustment specifies a time period during which stimulation occurs exactly one time through each of the channels of the implantable cochlear stimulator.

Thus, as can be seen, the present invention provides for the programming of the speech processor using the programmer unit, which programming implements several heretofore unavailable functions. Specifically, the present embodiment provides for the estimation of threshold and maximum comfortable stimulation levels based on objective measurements taken from the patient. In addition, the present embodiment provides for the display of a graphical audio spectrum analyzer, allowing the audiologist to effectively view the stimulation being applied through the electrode array and furthermore through a graphic equalizer to make real time adjustments to the gain applied on each channel, thereby modifying the stimulation applied on one or more channels.

Figure 3A:
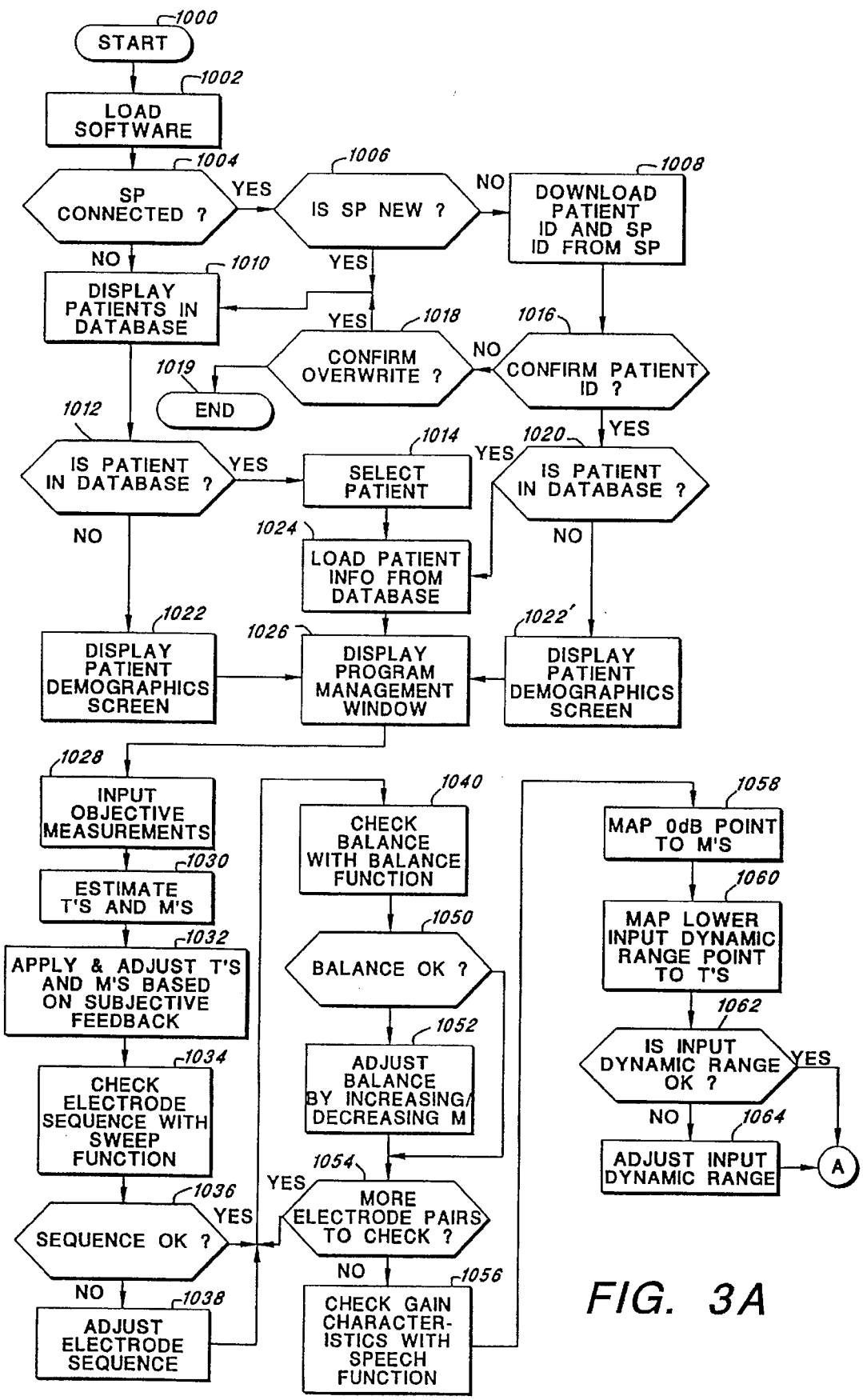
FIGS. 3A and 3B are a flow chart showing the steps traversed in order to program the components of FIG. 1 in accordance with one embodiment.
Figure 3B:
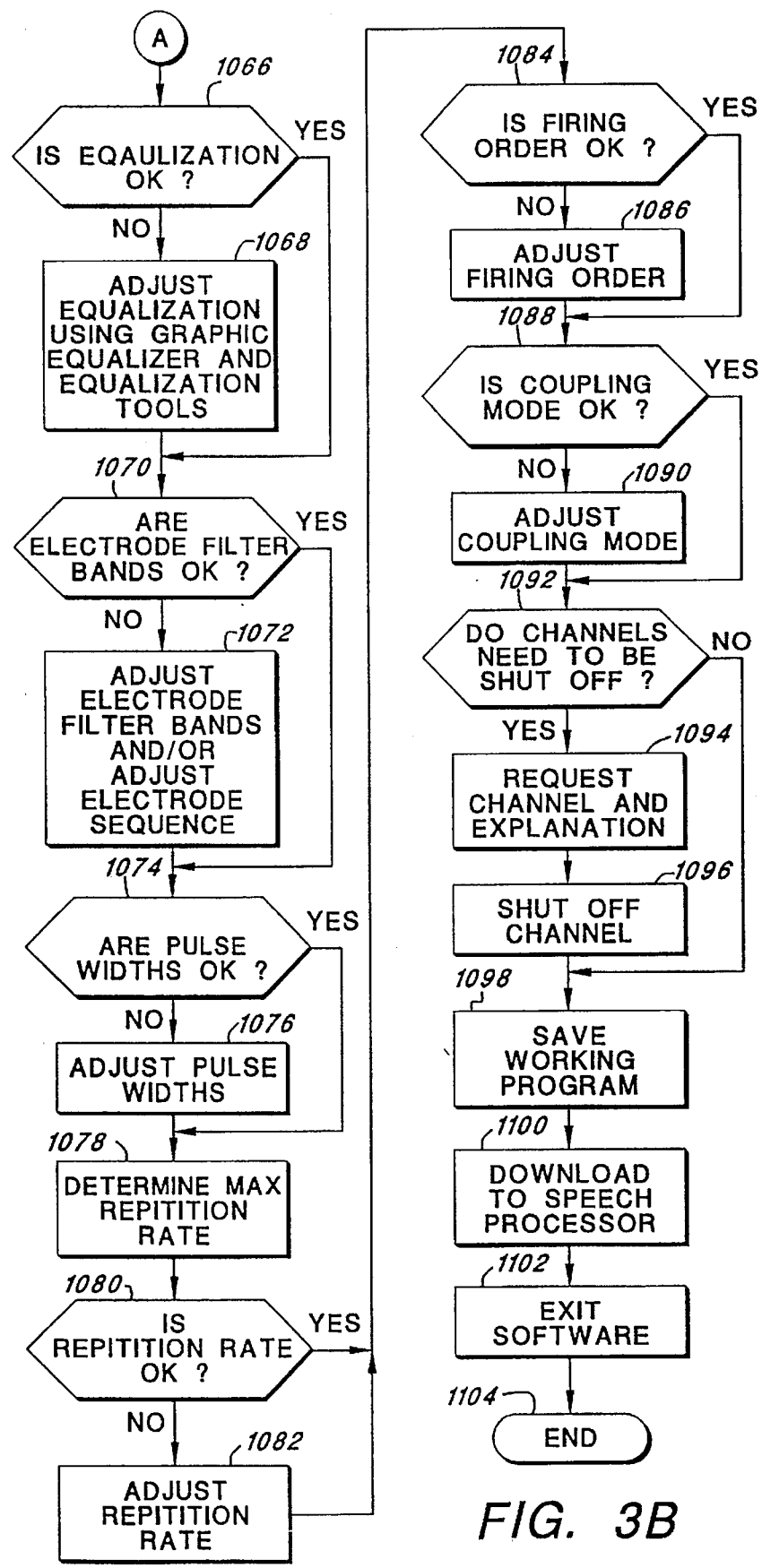

Referring next to FIGS. 3A and 3B, a flow chart is shown of the steps traversed in order to program the patient system 12 using the ICS fitting system 10 of the present embodiment. To begin a programming (or fitting) session (Block 1000), in accordance with the present embodiment, an audiologist loads (Block 1002) a software system (or programming) into the programmer unit 14. The software system may be programmed in an object oriented programming language such as VISUAL BASIC available from Microsoft Corporation of Washington. The software system directs the programmer unit 14 to query (Block 1004) an interface (not shown), e.g., a serial interface, for the presence of the speech processor 36 and clinician's programmer 22. An indication as to whether the speech processor 36 and clinician's programmer 22 are attached is made near the bottom of the display screen 16 on a status line. An indication is also made as to whether the implantable cochlear stimulator 46 is coupled to the speech processor 36, in response to a query signal from the speech processor 36 that is initiated by the programmer unit 14. In the event the speech processor 36 is coupled to the interface (Block 1004), a determination is made (Block 1006) as to whether the speech processor 36 is a new or "blank" speech processor, i.e., a speech processor that does not yet contain any programming for a particular patient. In the event the speech processor 36 is blank or new (Block 1006), the programmer unit 14 is directed to display (Block 1010) a list of patients in the patient database. In the event the speech processor is not detected (Block 1004), the list of patients in the patient database is also displayed (Block 1012). If the patient is in the patient database (Block 1012), the patient is selected (Block 1014) by name by the audiologist operating the programmer unit 14.

If after determining that the speech processor 36 is connected (Block 1004), the programmer unit determines that the speech processor is not new or blank (Block 1006), patient information stored in a memory (not shown) in the speech processor 36 is downloaded (Block 1008) from the speech processor into the programmer unit 14. The patient information may include the patient's name, the speech processor's serial number, the operating voltage of the speech processor 36, the current volume position of the speech processor 36, and the current selector switch position on the speech processor 36. After the patient information is downloaded from the speech processor 36 (Block 1006), the audiologist is asked to confirm that the patient information downloaded from the speech processor 36 matches the patient currently being fitted (Block 1016).

If the audiologist does not confirm that the patient information matches the patient being fitted (Block 1016), the audiologist is asked to confirm the overwriting of the programming in the speech processor 36 with information for the patient being fitted (Block 1018). If the audiologist confirms the overwriting of the programming in the speech processor (Block 1018), the list of patient names in the patient database is displayed (Block 1010), and if the patient being fitted is in the patient database (Block 1012), the audiologist selects (Block 1014) the patient being fitted by name from the database.

If the audiologist indicates that the patient is not in the patient database (Block 1012), after having had displayed (Block 1010) the list of patient names, a patient demographics screen is displayed (Block 1022). Similarly, if after a determination is made by the programmer unit (Block 1020) that the patient information, having being confirmed (Block 1016) by the audiologist as matching the patient being fitted, does not correspond to a patient in the patent database, a patient demographics screen is displayed (Block 1022'). An example of the patient demographics screen is shown in FIG. 5A. The patient demographics screen requests the patient's first and last names and middle initial; birthdate; patient ID number; street or P.O. box; city; state; zip code; country; home and work telephone numbers; insurance carrier; insurance ID number; and the following information relating to the left and right ears: etiology, progression, surgeon, surgery date, initial fitting date, onset age, profound deafness age, and implant serial number.

If the audiologist indicates that the patient is in the patient database (Block 1012), as mentioned above, he or she is asked to select a patient (Block 1014). Following the audiologist's selection (Block 1014), or following an automatic determination by the programmer unit 14 that the patient information matches a patient in the patient database (Block 1020), the programmer unit loads patient data including programming information from the patient database (Block 1024). Once the patient data is loaded from the patient database (Block 1024), or patient data is entered into the patient demographics screen (Block 1022 or Block 1022'), the audiologist is requested to indicate the fitting session and a program management window is displayed (Block 1026) by the programmer unit 14. The processes described above for retrieving the patient information and patient data are summarized in Table 1 and Table 2. In Table 1, "SP" means Speech Processor; "PT" means Pateient Present; and "DB" means the Data Base.

TABLE 1

| SP | PT | DB | DESCRIPTION | SYSTEM ACTION |
|---|---|---|---|---|
| Pat P | Pat P | Pat P | Existing Patient In Clinic. The Speech Processor connected to the clinician's work station belongs to Pat P. Pat P is sitting in the chair, and has records in the SCLIN database | The system asks the user to confirm that the patient name in the SP is the same as the patient sitting in the chair. If the user confirms, the system displays the patients name in the primary SCLIN window title bar and opens program management window for that patient. |
| Pat Q | Pat Q | Blank | Patient from another Clinic. The Speech Processor connected to the clinician's workstation belongs to Pat Q. Pat Q is sitting in the chair, but no record for Patient Q exists in the clinician's database. | The system displays the Patient Demographics dialog box. |
| Pat Q | Pat P | Pat P | Reassign old SP to New Patient. The Speech Processor connected to the | The system queries the user to ensure the user wants to overwrite the |

TABLE 1-continued

| SP | PT | DB | DESCRIPTION | SYSTEM ACTION |
|---|---|---|---|---|
| | | | clinician's workstation belongs to a patient not present in the office. The patient in the office has records in the clinician's database. | information in the connected Speech processor and assign it to the current patient. |
| Pat P | Any incorrect patient | Pat P | Wrong Patient/Reassign SP The Speech Processor connected to the clinician's workstation does not match the patient in the office, but does match a patient in the database. | The system queries the user to ensure the user wants to overwrite the information in the connected Speech processor and assign it to the correct patient. |
| blank | Pat P | Pat P | New SP The Speech Processor connected to the clinician's workstation does not contain any downloaded information. | The system displays no windows. The user must select a patient record to proceed. |
| Not Present | Pat P | Pat P | No Speech Processor Patient is in office but no SP is connected to the clinician's workstation. Patient record is present in the database. | The system allows access to all screens, but does not allow saving of any program changes. |
| Not Present | Pat P | blank | Patient is present, no database records exists and no speech processor is connected to the clinician's workstation. | The system displays no windows. The user must select a patient record to proceed. |
| Pat P | Not Present | Pat P | Fit by Mail Speech Processor is present but no patient is present | The system allows copying of existing programs to the SP but will not allow saving of any program changes. |
| Not Present | Default Patient | Default Patient | No Speech Processor is connected to the clinician's workstation, no patient is present. | The user can select the Practice patient from the Patient Select list. The user has access to all screens, but can save nothing and can not access a stimulation mode. Stimulate buttons are all grayed out. |
| blank | Pat P | blank | New Patient The Speech Processor is connected to the clinician's workstation, but contains no downloaded information. No record for this patient exists in the database. | The system displays the Patient Demographics dialog box. |

TABLE 2

| HARDWARE STATE | SYSTEM RESPONSE |
|---|---|
| SP is disconnected after a patient file has been established, impedances may or may not have been measured. | The System displays the Is your session complete dialog box. |
| SP is disconnected during download or while system is comminication with it. | The System displays the Cannot complete operation please plug the SP back in dialog box. When the SP is reconnected the dialog box goes away. |
| SP is connected, software is running, no patient file has been opened, ICS lock is not established. | The System reads the Info fromthe SP and opens patient file and displays that patient's Program Management window. |
| SP is connected, software is running and patient file different from the SP data is open, ICS lock is not established. | The System reads the Info from the SP and displays the Patient does not match dialog box. |
| SP is connected, software is running, no patient file has been opened, ICS lock is established. | The System measures impedances, reads the Info from the SP and opens patient file and Displays that Patient's Program Management window. |

The request of the audiologist to indicate the fitting session provides the audiologist with several choices for the fitting session: initial fitting, 3 months, 6 months, one year, 18 months, annual and interim visit. In the embodiment shown, the audiologist need only indicate the fitting session using the mouse or keyboard, as is commonly known in the art. Requiring that the audiologist indicate the fitting session is one example of a way in which the present embodiment assures compliance with governmental regulations, e.g., Food and Drug Administration regulations.

Once the patient is selected, and fitting session information has been entered, a program management screen is displayed which provides the audiologist with useful information as well as various options. The patient information, i.e., the patient's name and the speech processor's serial number, as retrieved from the speech processor, are shown, and the patient's name, as selected from the patient database is indicated at the top of the screen. Two default programs are generally shown, by way of example, in the program management window: continuous interleaved sampling (CIS) strategy, and compressed analog (CA) strategy. Other default programs, such as a flexible continuous interleaved sampling strategy program, may also be initially displayed on the program management screen.

Additional speech processing programs or strategies may also be stored in the patient database, and recalled and listed for the audiologist during each programming session. They may be loaded by the audiologist into the speech processor by "dragging," such as is known in the art, the desired program ID into the "POSITION 1," "POSITION 2," or "POSITION 3" boxes on the left side of the program management screen and "dropping" such as is also known in the art. The "POSITION 1," "POSITION 2," or "POSITION 3" boxes correspond to positions 1, 2 and 3 of the speech processor's selector switch. Thus, the program in the "POSITION 1" box will be implemented when the selector switch is on or position one, the program in "POSITION 2" when the selector switch is in position two, and so forth. In response to the "dragging" and "dropping" of a program into a memory in one of these boxes, the respective program is downloaded into the speech processor and associated with the respective switch position. Thus, the audiologist is able to quickly and easily transfer programs into the speech processor using a "drag and drop," interface, such as is known in the art.

Figure 5B:
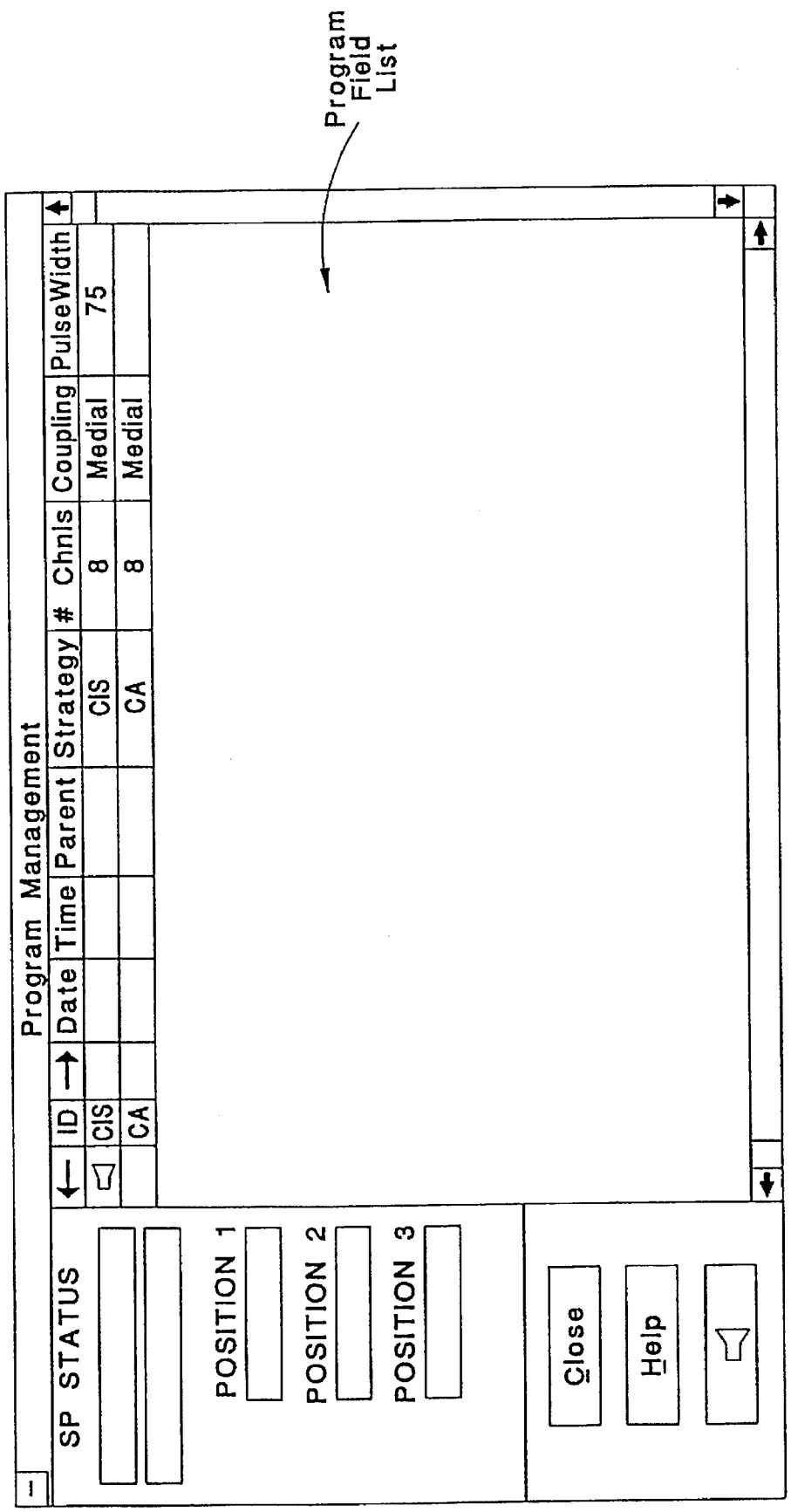
FIGS. 5A–5O show representative screen displays that may be generated as the invention is used to fit an ICS to a patient in accordance with the invention.

One program that is listed in the program management window is a "WRK" program or working program. The working program represents a temporary program under development by the audiologist. When the working program is saved, it is assigned the next available program ID number. The working program is the only program displayed on the program management screen that may be altered by the audiologist. Once a program is saved, and assigned an ID number, it is permanently stored in the patient database, and will be displayed on the program management screen every time the patient's record is accessed. FIG. 5B shows a close up view of the program management screen with the two default programs (CIS and CA) displayed.

Figure 5D:
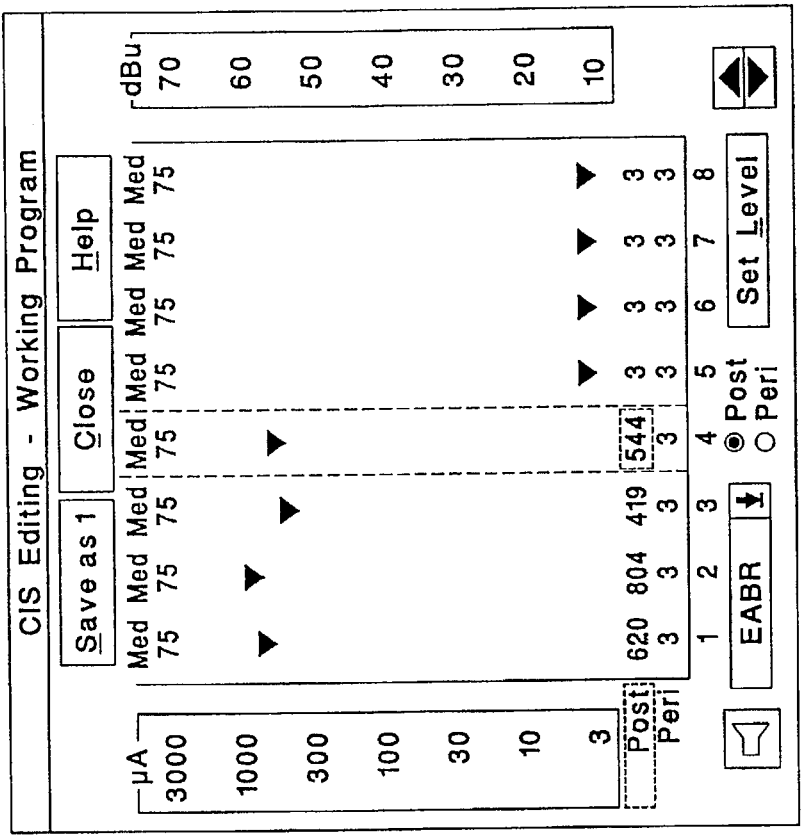
Figure 5C:
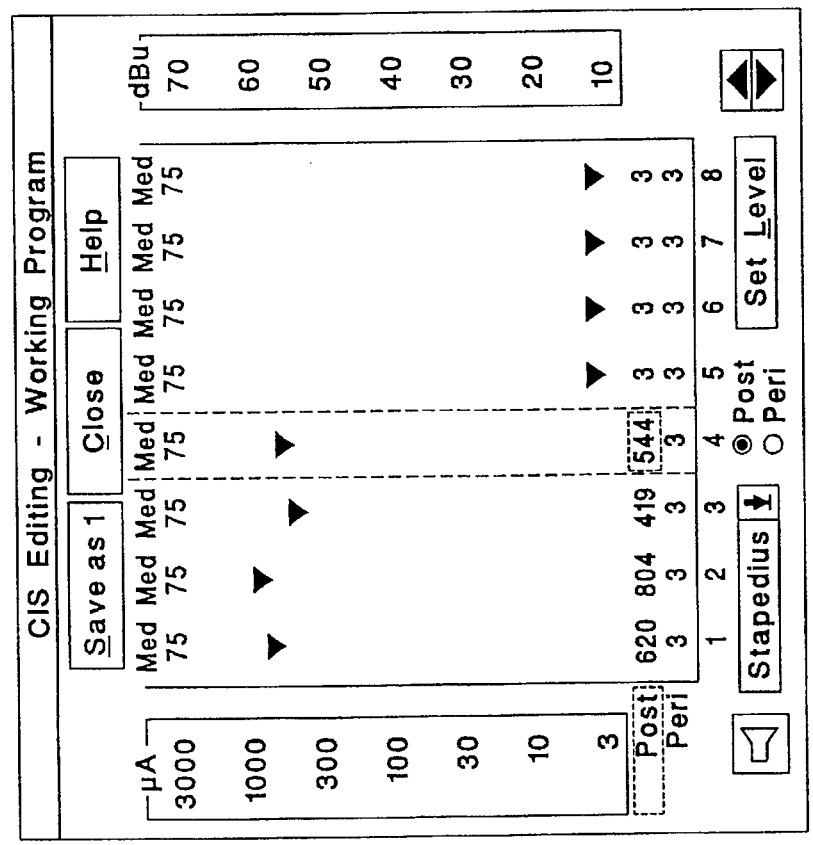

After the program management window is displayed (Block 1026, FIG. 3A), the audiologist preferably uses the system to make objective measurements using one or more objective measurement screens (Block 1028). Two examples of the types of objective measurement useful in the present embodiment are the stapedius reflex (either interoperative or postoperative), and the EABR, as described above. An example of an input screen for stapedius reflex and EABR measurements is shown in FIGS. 5C and 5D, respectively.

Based on these objective measurements, the programmer unit estimates (Block 1030, FIG. 3A) threshold stimulation levels (T's), and maximum comfortable stimulation levels (M's) for each of the channels of the implantable cochlear stimulator 46. These estimates are generated as described above.

Figure 5F:
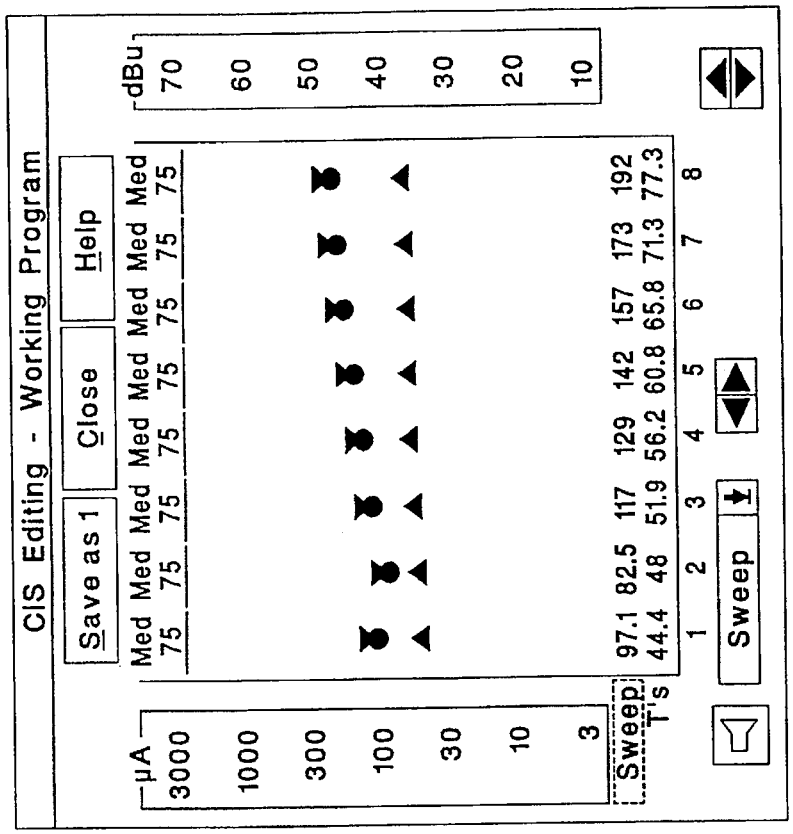
Figure 5E:
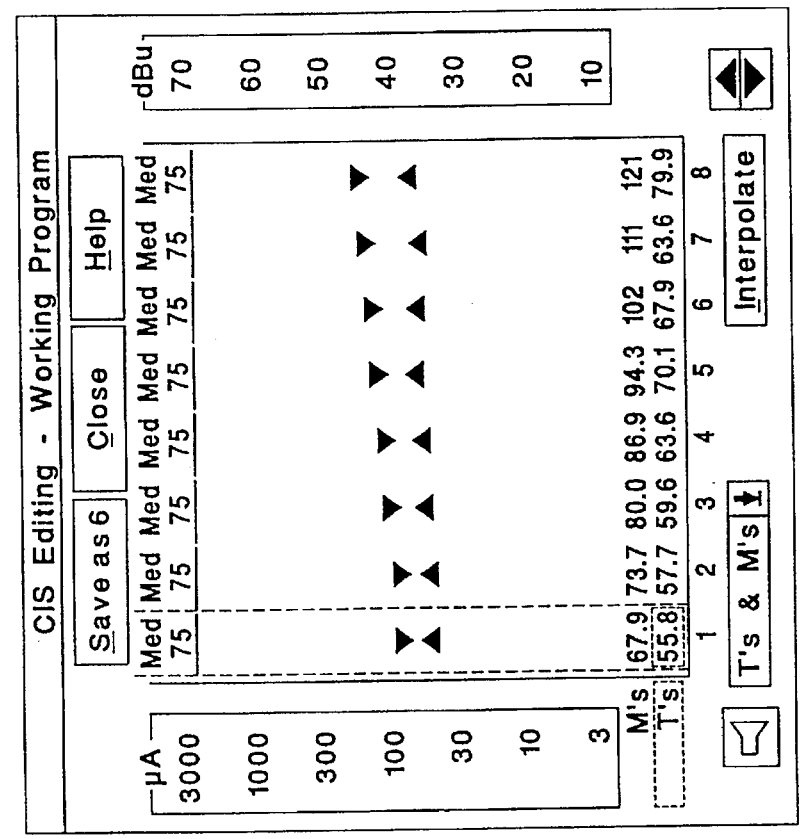

Next, stimulation currents are applied (Block 1032) at the estimated threshold stimulation levels and maximum comfortable stimulation levels for each channel of the implantable cochlear stimulator 46. The audiologist applies the stimulation currents by selecting either a threshold stimulation current or a maximum stimulation current for a channel, and then selecting a stimulation "button" on the programmer unit's screen display. Selection of the stimulation levels and the stimulation "button" is made using the digitizing device 20 or keyboard 18 (FIG. 1) to point to and select symbols on an editing screen representative of the threshold stimulation levels and maximum comfortable stimulation levels, and then to point to and select a stimulate "button" located near the lower left corner of the editing screen, as shown in FIG. 5E. The patient is then asked (Block 1032, FIG. 3A) by the audiologist whether the threshold stimulation levels and maximum comfortable stimulation levels, as estimated, are appropriate. Based on subjective feedback from the patient, the audiologist then adjusts, i.e., increases or decreases, (Block 1032) the stimulation levels by pointing to and selecting "up" or "down" arrows until the patient is subjectively satisfied with the stimulation level.

An example of the editing screen, for the continuous interleaved sampling strategy, showing the threshold stimulation levels, as upward-facing triangles, and the maximum stimulation levels, as downward-facing triangles, is shown in FIG. 5E. The channel being stimulated is shown highlighted, while the remaining channels are gray. The stimulate "button" is shown near the lower left corner of the editing screen, while the "up" and "down" arrows are shown near the lower right corner of the editing screen.

When no objective measurements are available, the threshold stimulation levels and the maximum stimulation levels are set to a very low value, e.g., 3 microamps, and subjective feedback, as described above, is relied upon to determine desired stimulation levels for two or more of the channels (Block 1032). Once the stimulation levels for two or more of the channels are set, the audiologist can select an interpolate "button," which causes the stimulation levels for the remaining channels to be approximated by interpolation. Adjustment (Block 1032) of the stimulation levels generated by interpolation is then made by the audiologist based on subjective feedback from the patient. The interpolate "button" is shown in the exemplary editing screen of FIG. 5E near the lower right hand corner of the editing screen to the left of the "up" and "down" arrows. When CA strategy is employed, sinusoidal stimulation at the center frequency is utilized to find the stimulation thresholds (T's) and maximum comfort thresholds (M's). If CIS strategy is employed, then a similar editing screen appears, except that in CIS strategy, pulsitle stimulation is used to find the T's and M's.

After the audiologist and patient have revised or established threshold and maximum comfortable stimulation levels for each of the channels of the implantable cochlear stimulator 46, the sequence of the electrodes is checked using a sweep function (Block 1034, FIG. 3A). An exemplary sweep screen is shown in FIG. 5F. Solid round dots represent the stimulation level to be applied during the sweep, which for the illustrated case are shown at the maximum comfortable stimulation levels. As with the editing screen discussed above, the stimulate "button" is located in the lower left corner of the sweep screen, and the "up" and "down" arrows used to adjust the stimulation levels are shown in the lower right corner of the sweep screen. "Left" and "right" arrows located near the bottom center of the sweep screen allow the audiologist to adjust the sweep direction, i.e., from the first electrode in the electrode array to the last, or vice versa.

To begin a sweep, the audiologist points to and selects the stimulate "button" and a stimulation current is applied to, e.g., the first channel in the electrode array. After stimulation current is applied to the first channel, stimulation current is applied to the second channel, and so forth until stimulation current is applied to the last channel. The process repeats itself until the audiologist deselects the stimulate "button." In response to this sequential stimulation, the patient should experience a hearing sensation that increases in pitch, or decreases in pitch, with each channel stimulated. If the patient "hears" tones out of sequence, this is an indication that the electrode placement within the cochlea may not be optimal, e.g., that the electrode array is folded over within the cochlea. In the event the tones are out of sequence (Block 1036), the electrode sequence can be altered (Block 1038), as described more fully below.

Figure 5L:
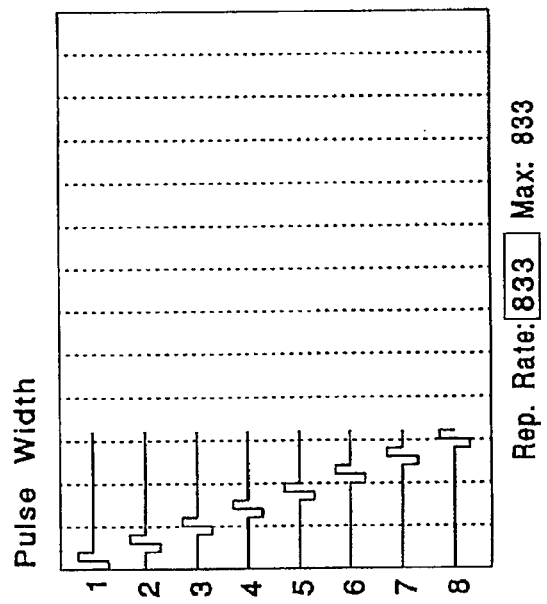
Figure 5G:
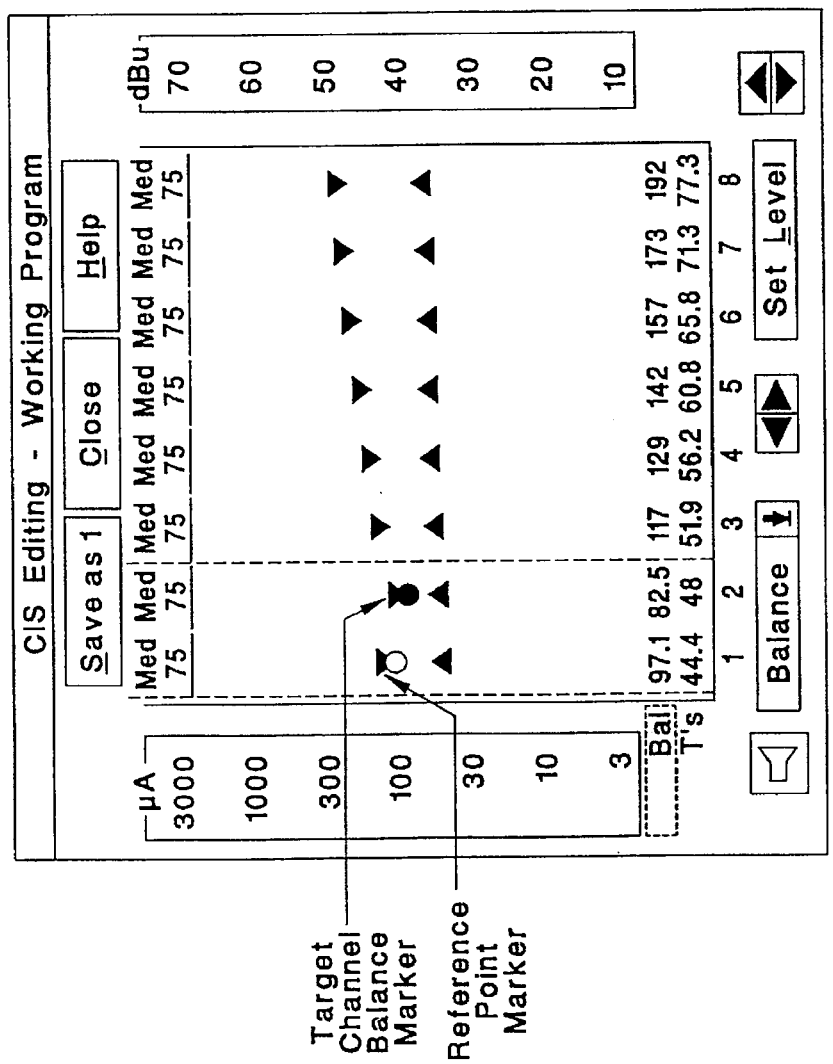

Once a proper ordering of the electrodes is achieved, the audiologist selects a balance screen (Block 1040, FIG. 3A) to balance the stimulation levels delivered on adjacent channels of the implantable cochlear stimulator. An exemplary balance screen is shown in FIG. 5G. An open dot is shown as a reference channel balance marker, and a closed or solid dot is shown as a target channel balance marker. In practice, the audiologist points to and selects the stimulate "button" in the lower left of the balance screen, which begins alternating stimulation of the reference and target channels, which are preferably adjacent channels. Based on subjective feedback from the patient, if the target channel "sounds" louder to the patient than the reference channel (Block 1050), the target channel marker is lowered (Block 1052) by pointing to and selecting the "down" arrow in the lower right corner of the balance screen; if the target channel "sounds" softer to the patient than the reference channel (Block 1050), the target channel balance marker is lowered (Block 1052) by pointing to and selecting the "up" arrow in the lower right corner of the balance screen. Once the target channel "sounds" about the same as the reference channel, the audiologist points to and selects the set level "button" to the left of the "up" and "down" arrows, and the maximum comfortable stimulation level for the target channel is adjusted to the stimulation level indicated by the target channel balance marker.

The target channel then becomes the reference channel, and the other channel adjacent to the target channel becomes the target channel. The above-described process is repeated (Blocks 1054 and 1040 et seq.) until balancing has been performed for all adjacent channels.

A speech screen is next selected by the audiologist (Block 1056, FIG. 3A). On the speech screen, a 0 dB line (or point) is mapped to the maximum comfortable stimulation levels. A lower line (or point), below the 0 dB line, dependent on an input dynamic range selected, is mapped to the threshold stimulation levels. When the stimulate "button" is pointed to and selected, the audiologist is able to stimulate the patient's cochlea by speaking into a microphone (not shown) on the headpiece (which houses the supercutaneous transmitter/receiver coil 42). When the audiologist speaks into the microphone, an audio spectrum of his or her speech is analyzed by frequency band and displayed on the speech screen. Any spectral bands containing sound levels at a certain point above the 0 dB line are clipped, and the patient is stimulated at the maximum comfortable stimulation level set in the editing, sweep, and balance screens. Using the audio spectrum analyzer, the audiologist is able to effectively see what the patient is hearing as the audiologist makes adjustments.

If the input dynamic range is too small/large (Block 1062), the lower line can be adjusted down/up by the audiologist (Block 1064) using the keyboard 18 or digitizing device 20 until the patient indicates that the input dynamic range is suitable. As presently configured, a default value of 60 dB is initially set. The adjustment from the default value is then made based on the subjective perception of the patient, and on the patient's ability to discriminate speech. In addition to or instead of the audiologist making adjustments to the input dynamic range, the patient may adjust the input dynamic range using the graphic equalizer board 28, described above. In this way the patient is directly able to evaluate and adjust the input dynamic range.

Another feature of the present embodiment is an on-screen graphic equalizer. If needed (Block 1066, FIG. 3B), the audiologist can adjust (Block 1068) the on-screen graphic equalizer, which adjusts gain on respective individual channels in the speech processor 36 by pointing to and selecting an equalizer bar associated with a particular channel, and then pointing to and selecting the "up" and "down" arrows to move the bar up for increased gain, and down for decreased gain. Gain can be adjusted from +10 dB to −10 dB in the present embodiment.

Figure 5M:
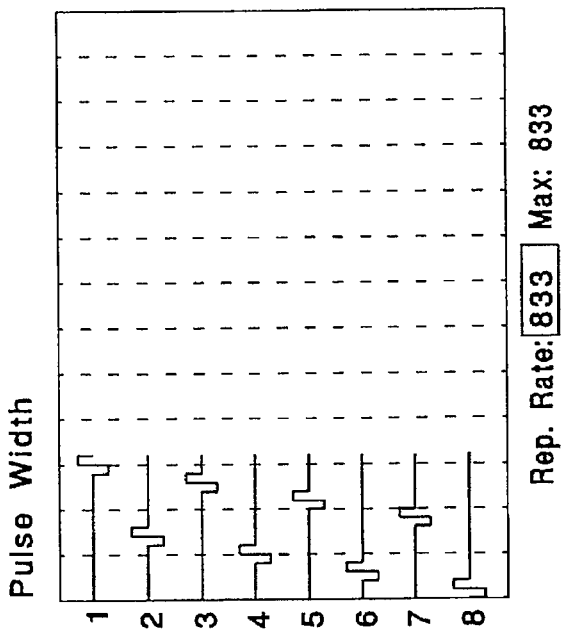
Figure 5H:
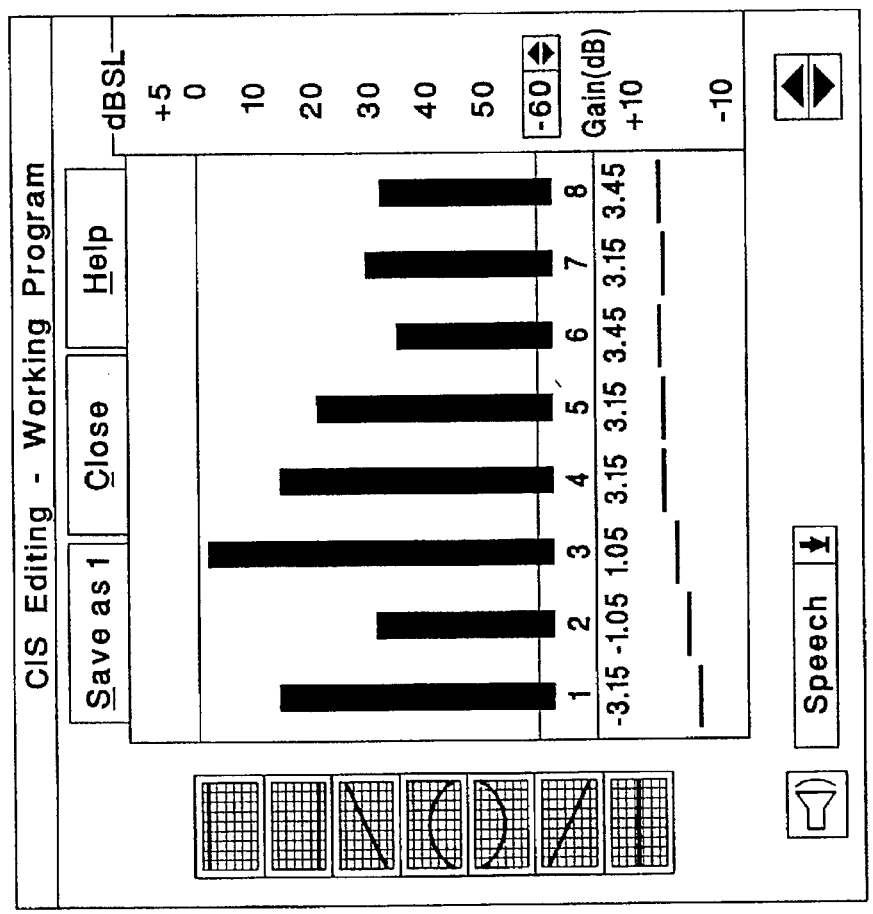

A set of "buttons" referred to as equalizer emphasis tools is located along the left edge of the speech screen, and can also be used to adjust the gain on the channels. Moving from top to bottom, as shown in FIG. 5H, the equalizer emphasis tools provide the following emphasis schemes: adjust up by 0.3 dB, adjust down by 0.3 dB, adjust high frequency band channels up and low frequency band channels down (i.e., high boost), adjust midrange band channels up and high and low frequency band channels down (i.e., midrange boost), adjust midrange band channels down and high and low frequency band channels up (i.e., high-low boost), adjust low frequency band channels up and high frequency band channels down (i.e., low boost), and move all equalizer bars to 0 dB (i.e, center). To use the equalizer emphasis tools, the audiologist points to and selects, using the digitizing device 20 or keyboard 18, the appropriate "buttons" in order to perform the desired emphasis. A speech screen is shown in FIG. 5H wherein the on-screen graphic equalizer has been used to adjust the gains on some of the channels. As can be seen in FIG. 5H, the equalizer bars, which are located across the middle of the speech screen below the audio spectrum analyzer, are set to cause slight (around 3 dB) amplification of the higher numbered channel and slight attenuation of the lower numbered channel.

In addition to, or instead of, the audiologist using the on-screen graphic equalizer to adjust channel gains, the patient may use the first eight slider-type equalizer potentiometers 30 of the graphic equalizer board 28 (FIG. 1) to adjust the channel gains. In this way, the patient is able to directly determine and adjust the channel gains to produce the most desirable, i.e., best "sounding", stimulations to the patient.

Figure 5I:
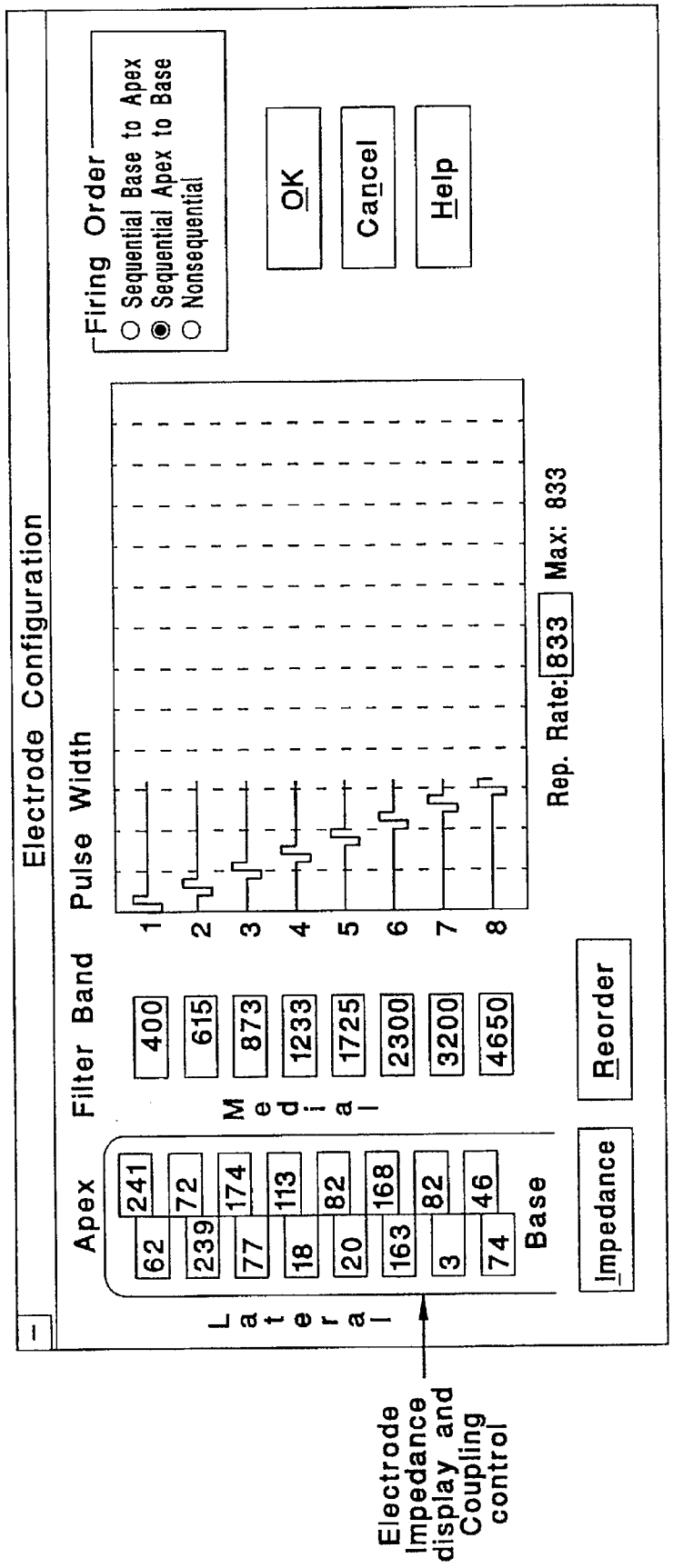
Figure 5K:
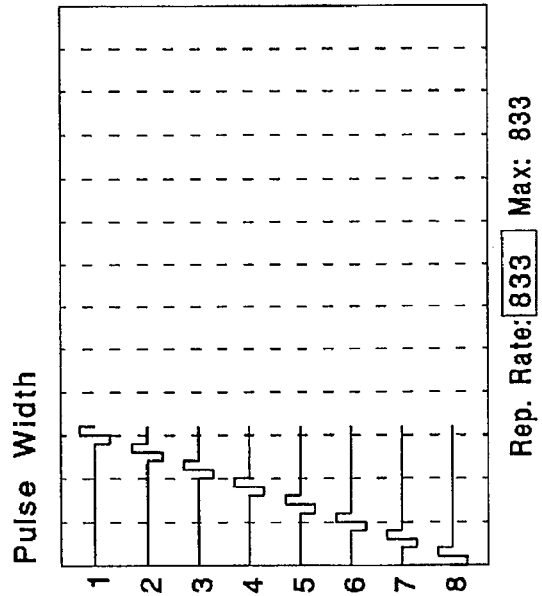
Figure 5J:
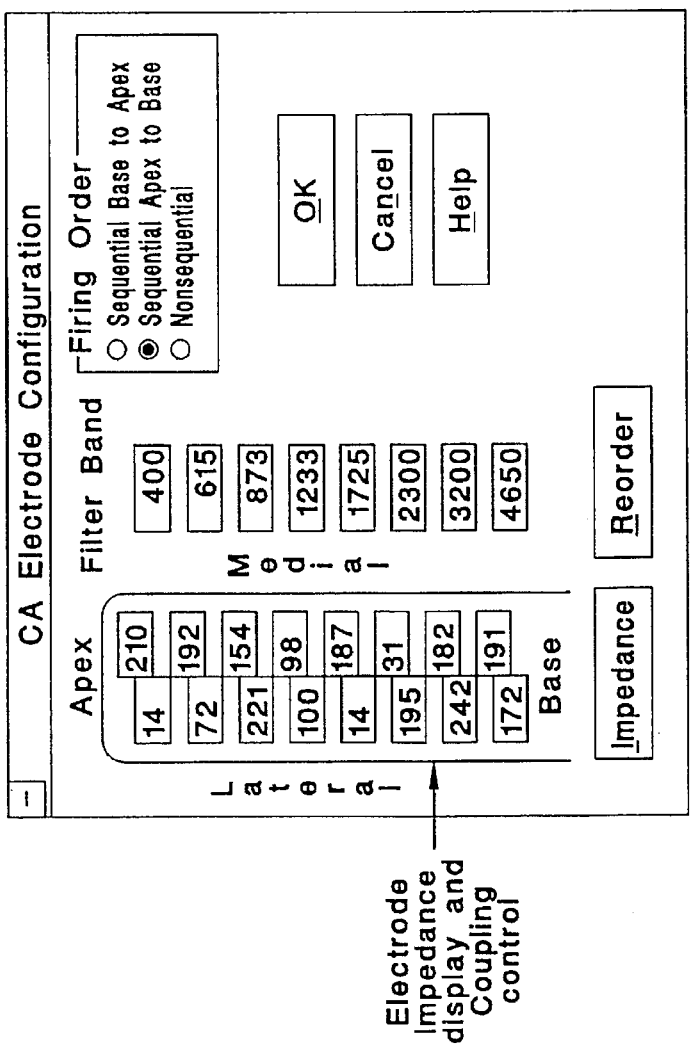

Several other adjustments are possible from an electrode configuration screen, such as is shown for the continuous interleaved sampling strategy in FIG. 5I. For example, the audiologist may "drag" a frequency band from one of the channels and "drop" it on another channel (Block 1072) if there is a perceived need to alter the frequency bands (Blocks 1070, 1072, FIG. 3B). The frequency band is assigned to the channel to which it has been "dragged", and the other frequency bands associated with the other channels automatically shift accordingly (Block 1072). In this way, the audiologist can easily reorder the spectral relationship of the electrodes and accommodate for conditions such as electrode array foldover. Adjustment of the frequency bands can, advantageously, be done in coordination with the sweep function, described above, so that when the sweep function detects an improperly ordered frequency band, the misordering can be remedied and retested immediately. A sample electrode configuration screen for the compressed analog strategy is shown in FIG. 5J.

A further adjustment that can be made, if needed (Block 1074), from the electrode configuration screen for the continuous interleaved sampling strategy, is pulse width. To adjust the pulse width for a channel, the audiologist points to and selects a respective pulse icon. When the desired pulse icon is selected, a menu appears which allows the audiologist to point to and select 75, 150, 225, or 300 milliseconds as the pulse width (Block 1076). As the desired pulse widths are selected for each channel, the programmer unit computes the maximum repetition rate for stimulation of each of the channels in sequence (Block 1078). This maximum repetition rate is initially set to a default rate based on the rate at which the electrode sequence is repeated. The rate is then systematically decreased, adding delay between the pulses. It is noted that some patients experience a low level buzz when this occurs. The repeition rate may be the source of such buzz. The higher the rate, the lower the intensity. By varying the rate, the clinican can determine whether the repetition rate is the source of the buzz.

Once the maximum repetition rate is computed, the audiologist then determines whether the current repetition rate is appropriate (Block 1080). If a change is desired in the current repetition rate, the audiologist enters (Block 1082) a current repetition rate in a repetition rate box located near the bottom of the electrode configuration window, as shown in FIG. 5I.

The audiologist may also adjust the firing order of the electrodes in the electrode array. Normally, the firing order will be from base to apex, i.e., from the highest pitches to the lowest pitches or from the highest numbered channels to the lowest numbered channels. However, in some patients, an apex to base firing order, or a nonsequential firing order may be desirable. If a change in firing order is desired (Block 1084), the audiologist points to and selects (Block 1086) the desired firing order using on screen "radio buttons," such as are known in the art. Options for firing order are depicted in the upper right corner of the electrode configuration screen shown at FIGS. 5I and 5J. The pulse width icons are preferably displayed on the electrode configuration screen in accordance with the selected firing order. For example, sequential base to apex firing is depicted using the pulse width icons shown in FIG. 5K. Sequential apex to base firing is depicted using the pulse width icons shown in FIG. 5L, and nonsequential firing is depicted as shown in FIG. 5M.

Another adjustment that can be made by the audiologist in the electrode configuration screen is the coupling mode. If a change in coupling mode on one or more channels is desired (Block 1088, FIG. 3B), the audiologist selects the channel by pointing to and selecting the electrode icons for the channel in the electrode array icon shown to the far left of the electrode configuration screen. Once the audiologist has pointed to and selected the desired electrode icon, a menu appears from which the audiologist can point to and select (Block 1090) either off, medial, lateral or bipolar coupling.

Depending on the coupling mode selected, the electrode icons in the electrode array icon are depicted as white or gray. If bipolar mode is selected, both electrodes of each electrode pair are depicted as white, because both electrodes are used in bipolar mode, as is known in the art. The electrode array icon of the electrode configuration screen is oriented so that lateral electrodes are depicted on the left side of the electrode array icon, and medial electrodes are depicted on the right side of the electrode array icon.

If the audiologist wishes to turn off one or more of the channels (Block 1092), he or she points to and selects the desired electrode pair within the electrode array icon, as described above. This causes the menu to appear, from which the audiologist points to and selects "off" (Block 1094). After the audiologist selects "off" the programmer unit displays a screen requesting (Block 1094) an explanation of why the channel is being turned off. The requirement that the audiologist enter an explanation before the channel is turned off is another example of how the programmer unit assures that governmental regulations are complied with, and specifically that Food and Drug Administration (FDA) regulations are complied with. The audiologist then points to and selects an explanation, using, e.g., "radio buttons," such as are known in the art, of why the electrodes for the selected channel are turned off (Block 1096).

Following the selection of a coupling mode for each channel, and possibly the selection of channels to turn off, the audiologist may save the working program (Block 1098), at which time the working program is assigned an ID number. Then the audiologist may download the program into the speech processor (Block 1100), as described above, by "dragging" the program number into one of the positions near the left of the program management screen. When the audiologist has finished saving any programs and/or downloading programs into the speech processor 36, he or she may exit the software system (Block 1102), and disconnect the speech processor from the programmer unit, thereby ending the current session (Block 1104).

Note that while the above description corresponds to steps in the flowchart of FIGS. 3A and 3B, it is to be understood that the audiologist has a great deal of discretion in ordering the steps involved in a fitting session. Thus, the above description and the flowchart of FIGS. 3A and 3B should be understood to represent one example of how a typical fitting session might proceed, however, it should further be understood that the above described steps, particularly those described in reference to Blocks 1028 through 1102, may be significantly reordered without the departing from the spirit and scope of the present invention.

Optionally (and not shown in FIGS. 3A and 3B), before exiting the software system or disconnecting the speech processor from the programmer unit, the audiologist may wish to have the patient compare two of the speech processing programs. A left speaker icon and a right speaker icon are present in the first and third columns of the program management screen. As shown, the left speaker icon is positioned next to the default CIS program, and the right speaker icon is positioned next to the working program. By depressing, for example, a left arrow key on the programmer unit's keyboard 18, the audiologist can instantly select, for example, the default CIS program, and similarly, by pressing a right arrow key can instantly select, for example, the working program. Up and down arrow keys can be used to move the left or right speaker icons from a currently selected program to a program above or below, respectively, the currently selected program.

In practice, the audiologist selects two programs to compare, moving the left speaker icon to the row of one of the programs, and the right speaker icon to the row of the other. Then, the audiologist stimulates the patient by pointing to and selecting the stimulate "button" near the lower left corner of the program management screen. By switching between the two programs, by depressing only the left or right arrow keys, the patient is given, effectively, a side-by-side comparison of two of the programs in the program management screen. Once the patient selects one of the two programs as being superior, further comparison can be made with other programs on the program management screen by moving, using the up and down keys, the appropriate speaker icon from the inferior program to the next program to be compared. In this way, the audiologist is able to quickly and easily exchange the programs operating in the speech processor 36 and is able to perform multiple comparisons between two, or conceivably more, programs, merely by toggling back and forth between such programs using keys on the keyboard 18.

Having above described the basic operation of the present embodiment, the following is a brief description of several additional features of the present embodiment of the invention. A speech processor log screen may be accessed by the audiologist pointing to and selecting a processor log icon "button" near the top of the program management screen. The processor log icon "button" may appear as a small icon that resembles the speech processor log screen. The speech processor log screen displays a summary record of download activity to speech processors serviced by a particular ICS fitting system 10. A download record is displayed in a far left column, or first column, showing the date and fitting session during which a program was downloaded into the speech processor. Second and third columns show the program ID number and corresponding creation date for the program downloaded, if any, into speech processor position one during the fitting session identified in column one. Similarly, fourth and fifth columns show the creation date for the program downloaded, if any, into speech processor position two during the fitting session identified in column one. Likewise, sixth and seventh columns identify the program number and creation date for the program downloaded, if any, into position three. A last column, column eight, identifies the serial number of the speech processor into which the downloading was performed during the fitting session identified in column one. All of the speech processor's positions receive a downloaded program during each programming session and therefore some of the columns on the speech processor log are blank. The speech processor log thus provides a comprehensive summary record of all of the downloading performed through a given programmer unit to particular speech processors. Advantageously, the processor log can be printed by pointing to and selecting a print report "button" located near the bottom of the processor log screen.

Another feature of the present embodiment is the provision of a context sensitive comments tool. The comments tool is activated by pointing to and selecting a comments icon "button", shown, for example, as a hand writing on paper. When the audiologist selects the comments icon "button", a comments screen appears, in which the audiologist can enter comments relevant to the patient or program. A program comments screen is displayed any time the comments icon "button" is selected while the editing screen, sweep screen, balance screen, or speech screen are active, i.e. have the "focus," as the term "focus" is used in the art. The program comments screen is also displayed when a comments field in the program management screen is selected by the audiologist. At all other times, selecting the comments icon "button" causes a patient comments screen to be displayed.

The audiologist is free to enter any information into the patient or program comments screen that he or she desires. Thus the patient and program comments screen provide a sort of free-form field in which the audiologist can take notes or place any other information he or she wishes to record relative to a patient or program. The current date and time can be inserted into the patient and program comments screens by the audiologist by pointing to and selecting a date and time icon "button" located near the lower right corner of the patient and program comments screens.

A session report may also be generated by the audiologist through selecting a report icon "button." The report icon "button" is located near the top center of the main screen display and appears as a printed piece of paper. Upon pointing to and selecting the report icon "button", a session report screen is displayed. The session report screen consists of several components including a program graph which shows the threshold stimulation levels and maximum comfortable stimulation levels. The stimulation levels, in µA, are shown on a logarithmic scale against the abscissa axis, and the channel number is represented along the ordinate axis. Also shown on the graph are the clipping levels plotted against the channel numbers. Clipping values are only set if the patient experiences pain on trial stimulation. If so, the clipping levels are reduced so that the effect does not occur.

Figure 5N:
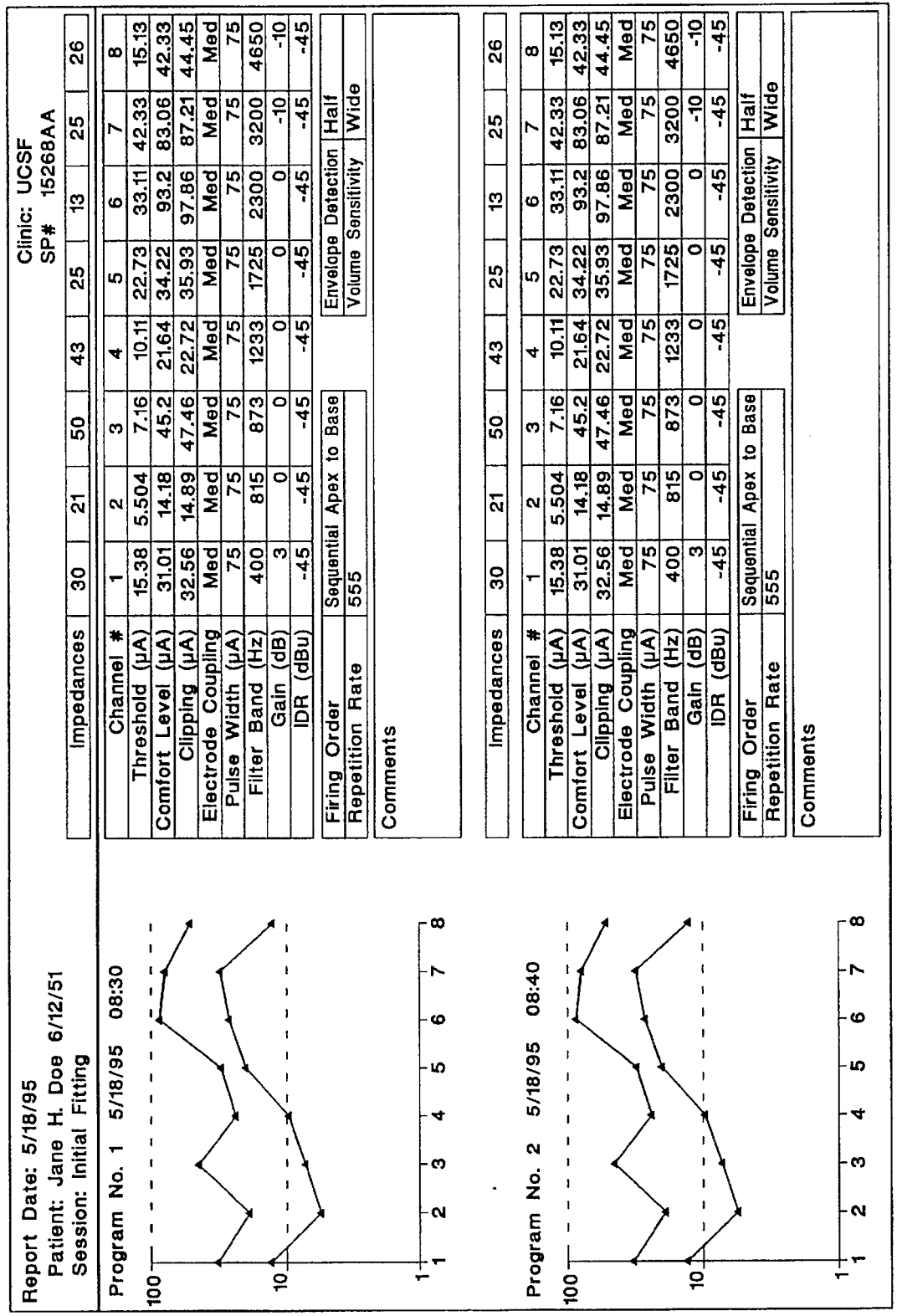

Also included in the session report screen are program data fields for each of the programs downloaded during the current fitting session. The program data fields include the threshold and maximum comfortable stimulation levels for each channel of the implantable cochlear stimulator, the clipping level for each channel, the electrode coupling mode and pulse width for each channel, the filter band of each channel, gain (as set by the graphic equalizer described above) and the Input Dynamic Range (IDR) for each channel, firing order, repetition rate, envelope detection and volume sensitivity. At present, the IDR is set to a global level for all channels. Further, it is noted that the volume sensitivity dictates the control the patient has with the volume control knob. For CIS, two options are presently available: wide (±5 dB) and narrow (±2 dB). The session report screen includes a print "button" generally in its lower left corner, which, when pointed to and selected, causes the generation of a printed session report. The printed session report is printed by a printer (not shown) coupled to the programmer unit 14. An example of a printed session report is shown in FIG. 5N.

There are also several "options" screens that can be selected by the audiologist. A first option screen allows the audiologist to indicate the elements he or she wants displayed on the program management screen. A second option screen allows the audiologist to select the elements he or she wants displayed in the processor log. Other options relate to the continuous interleaved sampling strategy, such as the envelope detection scheme; volume range; signal off time, i.e., the time during which stimulation signals are not applied to any channel of the implantable cochlear stimulator following application of a stimulation current, for the editing screen, the sweep screen and the balance screen; pause time, i.e., the time between sequences for the sweep screen and the balance screen; "alt" increment (at present a minimum increment of 0.38 dB, or a setable increment of 0.38 to 2 dB, is available); and cutoff frequency of a lowpass filter used to remove extraneous information ater the envelope (channel) detection.

Similarly, options relating to the compressed analog (CA) strategy may also be set, such as the signal off time, i.e., the time during which stimulation signals are not applied to any channel of the implantable cochlear stimulator following application of a stimulation current, for the editing screen, the sweep screen and the balance screen; pause time for the sweep screen and the balance screen; alt increment; and volume range; as explained previously.

Various general operating parameters may also be entered into a general options screen. These general operating parameters include the location of archive files, the location of import files, and an alternative file location. Generally, the first two of these parameters will be set to indicate a removable media, such as a floppy disk drive, and the third will be set to indicate a fixed media, such as a hard disk drive. The general operating parameters also include the name of the user, i.e., the audiologist, and the name of the clinic where the programmer unit is used.

A stapedius reflex options screen, shown in FIG. 5O, allows the audiologist to set various adjustment factors for the CIS and CA strategies in order to adjust the maximum comfortable stimulation level (M) and threshold stimulation level (T) for use with these strategies.

By adjusting the options screens, the audiologist is thus able to greatly manipulate and customize the operation of the programmer unit. It is contemplated that as other strategies, such as flexible continuous interleaved sampling strategy, come into use, that the software system described herein is readily modifiable to accommodate programming in accordance with such strategies. Thus, the present invention provides a highly flexible and adaptable system and method for programming or fitting a speech processor for an implantable cochlear stimulator.

Figure 4:
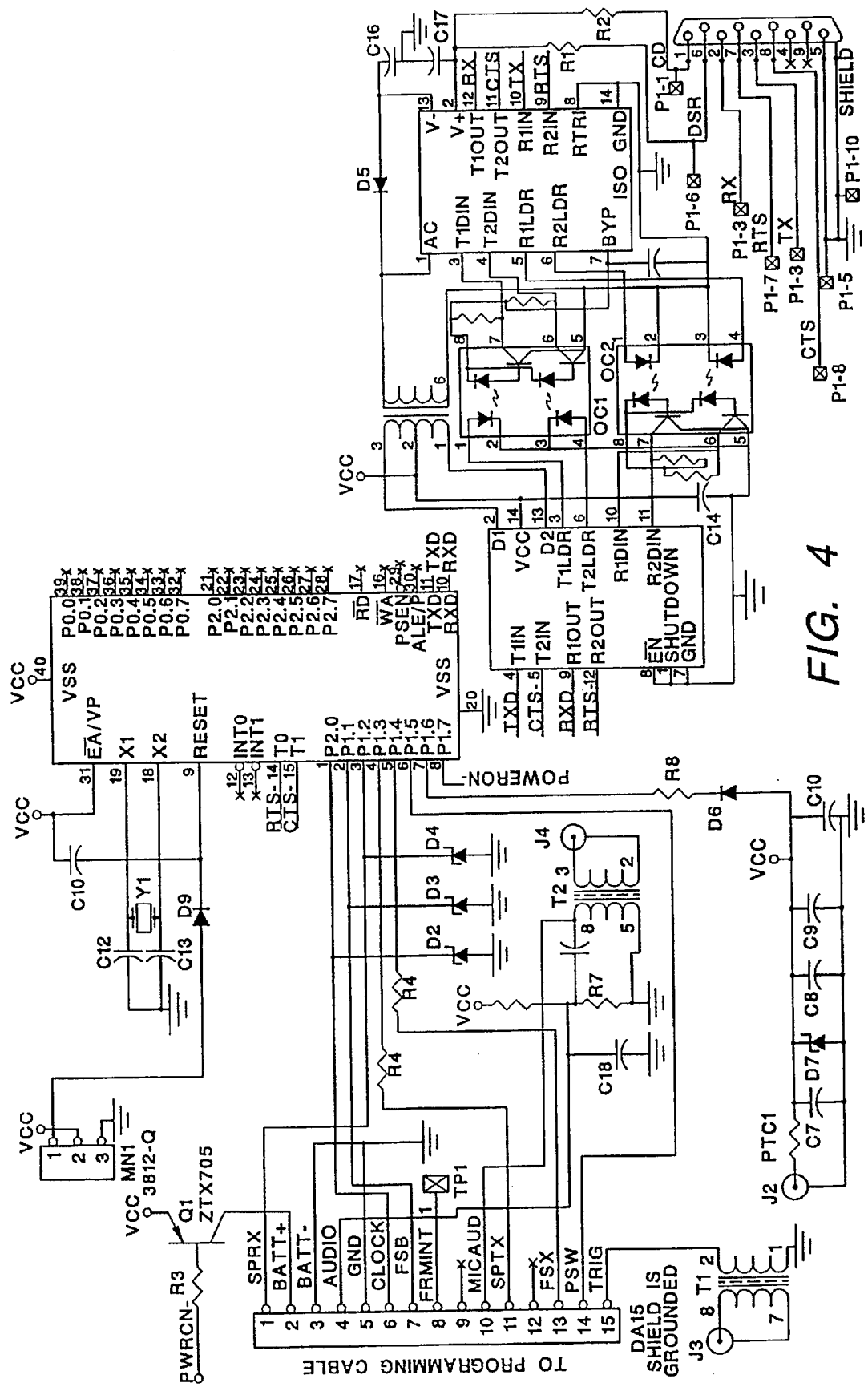
FIG. 4 is a schematic diagram showing a clinician's programmer that may be used with the embodiment of FIG. 1.

Referring next to FIG. 4, a schematic diagram is shown of the clinician's programmer 22. The clinician's programmer 22 serves as a protocol converter and an interface between a standard serial interface; preferably within the programmer unit 14, and the proprietary serial interface of the speech processor 36. It is envisioned that the clinician's programmer 22 will either be easily reprogrammed or adapted for use with other proprietary serial interfaces, or that a separate clinician's programmer will be used for each type of interface found on speech processors. The schematic diagram provided will enable one skilled in the art to make and use the clinician's programmer 22 as described herein, and therefore further explanation of the clinician's programmer is not presented.

While the invention herein disclosed has been described by means of specific embodiments and applications thereof, numerous modifications and variations could be made thereto by those skilled in the art without departing from the scope of the invention set forth in the claims.

What is claimed is:

1. A method of fitting an auditory stimulation system, the stimulation system including an implanted unit and a programmer unit; the implanted unit having means for generating a stimulating current and at least one electrode channel associated therewith through which said stimulating current is applied to a patient, said at least one electrode channel having a gain associated therewith and means for adjusting the gain within limits so that the magnitude of the stimulating current may be adjusted; and the programmer unit having coupling means for coupling it to the implanted unit, storage means for storing information, prompting means for prompting entry of specified information, and entry means for entering information into the storage means, the method comprising:

coupling the programmer unit to the implanted unit implanted in the patient;

detecting whether demographic information of the patient is stored in a patient database stored in the storage means of the programmer unit, and if not prompting an operator of the programmer unit to enter demographic information of the patient for storage in the patient data base;

prompting the operator to enter a fitting session for the patient;

entering the fitting session into the storage means of the programmer unit, whereby a record is made within the storage means that the patient was fitted during the entered fitting session;

prompting the operator to enter an objective measurement;

receiving the objective measurement into the programmer unit; and determining an initial threshold stimulation current for the at least one electrode channel of the implanted unit as a function of the objective measurement.

2. The method of claim 1 wherein said prompting includes prompting said operator to enter a stapedius reflex measurement of the patient, said receiving includes receiving the stapedius reflex measurement into the programmer unit, and said determining includes determining the initial threshold stimulation current as a function, at least in part, of the stapedius reflex measurement.

3. The method of claim 1 wherein said prompting includes prompting said operator to enter an electrically elicited auditory brainstem response (EABR) measurement of the patient, said receiving includes receiving the EABR measurement into the programmer unit, and said determining includes determining the initial threshold stimulation current as a function, at least in part, of the EABR measurement.

4. The method of claim 1 further including assisting the operator in making the objective measurement by prompting the operator through the prompting means of specific types of objective measurements the operator may make.

5. The method of claim 1 wherein said determining includes determining a most comfortable stimulation current for the at least one electrode channel as a function of said objective measurement.

6. The method of claim 1 further including:

stimulating said patient through said implanted unit using said initial threshold stimulation current on said at least once electrode channel;

receiving subjective feedback from said patient regarding said stimulating using the initial threshold stimulation current; and adjusting said initial threshold stimulation current for said at least one electrode channel in response to the subjective feedback received from said patient, and generating an adjusted threshold stimulation current in response thereto.

7. The method of claim 6 further including:

determining an initial most comfortable stimulation current for said electrode channel as a function of said objective measurement;

stimulating the patient through the implanted unit using the initial most comfortable stimulation current on the at least one electrode channel;

receiving subjective feedback from the patient regarding said stimulating using the initial most comfortable stimulation current; and adjusting the initial most comfortable stimulation current for the electrode channel in response to the subjective feedback from the patient, and generating an adjusted most comfortable stimulation current in response thereto.

8. The method of claim 7 wherein the stimulation system further includes display means for displaying the specified information, the method further including:

mapping a lower stimulation level determined by an estimated input dynamic range to said adjusted threshold stimulation current, said estimated input dynamic range defining a range of sound amplitudes that cause stimulation currents to be appplied through the at least one electrode channel to stimulate the patient;

mapping a zero decibel (0 dB) reference level to said adjusted initial most comfortable stimulation current, said 0 dB reference level defining a maximum stimulation current that may be applied to stimulate the patient through the at least one electrode channel;

stimulating said patient through said at least one electrode channel with a speech stimulation current that varies as a function of a speech signal; and displaying a graphical representation using said programmer unit, said graphical representation including a comparative display of said speech signal, said estimated input dynamic range, and said 0 dB reference level.

9. The method of claim 8 including:

receiving speech signal subjective feedback from the patient relative to the stimulating performed using the speech stimulation current corresponding to the speech signal;

adjusting said estimated input dynamic range in response to the speech signal subjective feedback, and generating an adjusted input dynamic range in response thereto; and adjusting the gain of said at least one electrode channel in response to the speech signal subjective feedback, and generating an adjusted gain in response thereto.

10. The method of claim 8 including:

receiving speech perception performance data from the patient relative to the stimulating performed using the speech stimulation current corresponding to the speech signal;

adjusting said estimated input dynamic range in response to the speech perception performance data received from said patient, and generating an adjusted input dynamic range in response thereto; and adjusting the gain of said at least one electrode channel in response to speech perception performance data received from said patient, and generating an adjusted gain in response thereto.

11. The method of claim 1 including storing said objective measurement in the storage means of said programmer unit.

12. A method of fitting an auditory stimulation system, the stimulation system including an implanted unit and a programmer unit; the implanted unit having means for generating a stimulating current and a plurality of electrode channels through which a respective stimulating current may be applied to a patient, each of said plurality of electrode channels having a gain associated therewith and means for adjusting the gain so that the magnitude of the stimulating current applied through the channel may be adjusted within limits; and the programmer unit having coupling means for coupling it to the implanted unit, storage means for storing information, a patient data base stored in the storage means, prompting means for prompting entry of specified information, display means for displaying specified information, and entry means for entering information into the storage means, the method comprising:

coupling the programmer unit to the implanted unit;

detecting whether demographic information of the patient is stored in the patient database, and if not prompting an operator of the programmer unit to enter demographic information of the patient for storage in the patient data base;

prompting the operator to enter a fitting session for the patient;

entering the fitting session into the storage means of the programmer unit, whereby a record is made within the storage means that the patient was fitted during the entered fitting session;

stimulating the patient with a stimulating current through at least one of the plurality of electrode channels, the stimulating current being a function of a speech signal;

displaying, in real time, a graphical representation of the speech signal using the programmer unit;

adjusting the gain of the respective electrode channel through which the stimulating current is being applied, while viewing the graphical representation of the speech signal, thereby providing an adjusted stimulating current, until the patient perceives the adjusted stimulating current is at a most comfortable stimulation level, thereby providing a most comfortable stimulating current.

13. The method of claim 12 including:

mapping a lower sound stimulation level determined by an estimated input dynamic range to said adjusted stimulation current, said estimated input dynamic range defining a range of sound amplitudes that cause stimulation currents to be appplied through the at least one electrode channel to stimulate the patient;

mapping a zero decibel (0 dB) reference level to the most comfortable stimulating current, said 0 dB reference level defining a maximum stimulating current that may be comfortably applied to stimulate the patient through a respective one of said plurality of electrode channels; and displaying the estimated input dynamic range and the zero decibel reference level along with the graphical representation of the speech signal, using the programmer unit.

14. The method of claim 13 including:

prompting an operator to enter an objective measurement;

receiving the objective measurement into said programmer unit;

storing the objective measurement in said storage means;

determining an estimated threshold stimulation current for at least one of the plurality of electrode channels of said implanted unit as a function of the objective measurement; and determining an estimated comfortable stimulation current for said electrode channel as a function of the objective measurement.

15. The method of claim 14 including:

stimulating said patient through said implanted unit using said estimated threshold stimulation current on said at least one of said plurality of electrode channels;

receiving subjective feedback from said patient regarding said stimulating using the estimated threshold stimulation current;

adjusting said estimated threshold stimulation current for said at least one electrode channel in response to the subjective feedback received from said patient;

stimulating said patient through said implanted unit using said estimated comfortable stimulation current on said at least one of said plurality of electrode channels;

receiving subjective feedback from said patient regarding said stimulating using the estimated comfortable stimulation current; and adjusting said estimated comfortable stimulation current for said at least one electrode channel in response to the subjective feedback received from said patient.

16. A method of fitting an auditory stimulation system, the stimulation system including an implanted unit and a programmer unit; the implanted unit having means for generating a stimulating current and at least one electrode channel through which a respective stimulating current may be applied to a patient, said at least one electrode channel having a gain associated therewith and means for adjusting the gain within limits so that the magnitude of the stimulating current applied through the channel may be adjusted; and the programmer unit having coupling means for coupling it to the implanted unit, storage means for storing information, a patient data base stored in the storage means, prompting means for prompting entry of specified information, entry means for entering information into the storage means, and display means for displaying specified information, the method comprising:

coupling the programmer unit to the implanted unit implanted in the patient;

detecting whether demographic information of the patient is stored in the patient database;

in the event the demographic information is not detected as being in the patient database, prompting an operator of the programmer unit through the prompting means to enter the demographic information and receiving the demographic information into the storage means of the programmer unit;

prompting the operator to enter a fitting session;

entering the fitting session into the storage means of the programmer unit, whereby a record is made within the storage means that the patient was fitted during the entered fitting session;

prompting the operator to enter an objective measurement;

receiving the objective measurement into the programmer unit;

storing the objective measurement in the storage means;

determining an estimated threshold stimulation current for the at least one electrode channel of the implanted unit as a function of the objective measurement, where said estimated threshold stimulation current represents a stimulation current of sufficient magnitude intended to be perceived by the patient;

determining an estimated comfortable stimulation current for the at least one electrode channel as a function of the objective measurement, where said estimated comfortable stimulation current represents a stimulation current of a maximum magnitude that is intended to be comfortably perceived by the patient;

stimulating the patient using the estimated threshold stimulation current on the at least one electrode channel;

receiving subjective feedback from said patient relative to whether the stimulating using the estimated threshold stimulation current on the at least one electrode channel is perceived;

adjusting the estimated threshold stimulation current using the means for adjusting the gain of the at least one electrode channel in response to the subjective feedback received from the patient, thereby providing an adjusted threshold stimulation current;

stimulating the patient using the estimated comfortable stimulation current on the at least one electrode channel;

receiving subjective feedback from said patient relative to whether the stimulating using the estimated comfortable stimulation current on the at least one electrode channel is comfortably perceived;

adjusting the estimated comfortable stimulation current for the at least one electrode channel in response to the subjective feedback received from the patient, thereby providing an adjusted comfortable stimulation current;

mapping an estimated input dynamic range to the adjusted threshold stimulation current, said estimated input dynamic range defining a range of sound amplitudes that cause stimulation currents to be apppplied through the at least one electrode channel to stimulate the patient;

mapping a zero decibel (0 dB) reference level to the adjusted comfortable stimulation current, said 0 dB reference level defining a maximum stimulation current that may be comfortably applied to stimulate the patient through the at least one electrode channel, the input dynamic range being measured relative to the 0 dB reference level;

stimulating the patient through the at least one electrode channel with a variable stimulation current that varies as a function of a speech signal;

displaying a graphical representation of the speech signal, along with the estimated input dynamic range and the 0 dB reference level, using the display means of the programmer unit;

receiving subjective feedback from the patient relative to the stimulating using the variable stimulation current;

adjusting the estimated input dynamic range in response to the subjective feedback received from the patient relative to the stimulating with the variable stimulation current that varies as a function of the speech signal, and generating an adjusted input dynamic range in response thereto; and adjusting the gain of the at least one electrode channel in response to the subjective feedback received from the patient relative to the stimulating with the variable stimulation current that varies as a function of the speech signal, and generating an adjusted gain in response thereto.

17. An apparatus for fitting a patient with an implantable cochlear stimulator (ICS), the ICS including means for generating stimulation currents and at least one electrode channel having an electrode channel gain associated therewith through which stimulation currents may be applied to the patient, the fitting apparatus comprising:

a programmer unit (14) comprising:

a data entry device (18);

means for coupling the programmer unit with the ICS, whereby data may be transferred between the programmer unit and the ICS;

memory means for storing a patient data base, said patient data base including demographic information, as well as stimulation parameters, for a plurality of patients, each of whom uses an ICS;

means for prompting entry of demographic information using the data entry device if the demographic information is not detected in the data base;

means for prompting entry of an objective measurement using the data entry device for the patient who is to be fitted using the programmer unit;

means for receiving the objective measurement into the memory circuit of the programmer unit;

means for determining an estimated threshold stimulation current for the at least one electrode channel of the ICS as a function of the objective measurement;

means for determining an estimated comfortable stimulation current for said at least one electrode channel as a function of said objective measurement;

means for adjusting the estimated threshold stimulation current and the estimated comfortable stimulation current to produce an adjusted threshold stimulation current and an adjusted comfortable stimulation current to be used by the ICS of the patient;

means for storing the adjusted threshold stimulation current and the adjusted comfortable stimulation current in the patient data base stored in the memory means of the programmer unit; and means for transferring the adjusted threshold stimulation current and the adjusted comfortable stimulation current to the ICS of the patient, whereby the adjusted threshold stimulation current and the adjusted comfortable stimulation current may thereafter be used by the ICS.

18. The apparatus of claim 17 wherein the coupling means includes:

a clinician's programmer (22) comprising:

a first serial interface coupled to the programmer unit (14);

a second serial interface including means for interfacing the clinician's programmer to the ICS;

protocol converter means for converting a first data protocol used by the first serial interface to a second data protocol used by the second serial interface as data is transferred between the programmer unit and the ICS.

19. The apparatus of claim 17 wherein said coupling means further comprises an equalizer board (28) coupled to the programmer unit (14) through the clinician's programmer (22).

20. The apparatus of claim 19 wherein said equalizer board includes:

at least one potentiometer connected thereto for adjusting the electrode channel gain on the at least one electrode channel of said ICS.

21. The apparatus of claim 20 wherein said equalizer board includes:

at least one potentiometer connected thereto for adjusting an input dynamic range of the ICS, said input dynamic range defining a range of stimulation currents that may be generated at levels between the adjusted threshold stimulation level and the adjusted comfortable stimulation level.

22. The apparatus of claim 21 wherein said equalizer board includes:

a first potentiometer connected thereto for adjusting electrode channel gain on at least one electrode channel of said implantable cochlear stimulator; and a second potentiometer connected thereto for adjusting the input dynamic range of said ICS.

23. The apparatus of claim 22 wherein said first potentiometer and said second potentiometer are slider-type potentiometers.

24. An apparatus for fitting a patient with an implantable cochlear stimulator (ICS), the ICS including means for generating stimulation currents and at least one electrode channel having an electrode channel gain associated therewith through which stimulation currents may be applied to the patient, the fitting apparatus comprising:

a programmer unit comprising:

a display device;

means for coupling the programmer unit with the ICS, whereby data may be transferred between the programmer unit and the ICS;

memory means for storing a patient data base, said patient data base including demographic information, as well as stimulation parameters, for a plurality of patients, each of whom uses an ICS;

means for prompting entry of demographic information if the demographic information is not detected in the data base;

means for generating a speech signal;

means for determining an estimated threshold stimulation current for the at least one electrode channel of the ICS that defines a lower limit of stimulation currents that can be perceived by the patient;

means for determining an estimated comfortable stimulation current for the at least one electrode channel that defines an upper limit of stimulation currents that can be comfortably perceived by the patient;

means for causing the (ICS) to stimulate the patient with a variable stimulation current derived from the speech signal, said variable stimulation current having a magnitude that lies within a range between the estimated threshold stimulation current and the estimated comfortable stimulation current;

means for displaying, in real time, a graphical representation of the speech signal using the display device of the programmer unit; and means for adjusting the estimated threshold stimulation current and the estimated comfortable stimulation current to produce an adjusted threshold stimulation current and an adjusted comfortable stimulation current that may be used to set new upper and lower limits for the variable stimulation current that are fitted to what the patient comfortably perceives.

25. The apparatus of claim 24 wherein said programmer unit further comprises:

means for mapping an estimated input dynamic range to the adjusted threshold stimulation current, said estimated input dynamic range defining a range of sound amplitudes that cause stimulation currents to be applied to the patient between the adjusted threshold stimulation level and the adjusted comfortable stimulation level;

means for mapping a zero decibel (0 dB) reference level to the adjusted comfortable stimulation current, the 0 dB reference level defining a maximum stimulation current that may be applied to comfortably stimulate the patient through the at least one electrode channel, the input dynamic range being measured relative to the 0 dB reference level; and means for displaying the estimated input dynamic range and the 0 dB reference level, along with said graphical representation of the speech signal.

26. The apparatus of claim 25 wherein said coupling means includes a clinician's programmer comprising:

a first serial interface coupled to the programmer unit;

a second serial interface including means for interfacing the clinician's programmer to the ICS;

protocol converter means for converting a first data protocol used by the first serial interface to a second protocol used by the second serial interface as data is transferred between the programmer unit and the ICS.

27. The apparatus of claim 26 wherein said coupling means further comprises an equalizer board coupled to the programmer unit through the clinician's programmer.

28. The apparatus of claim 27 wherein said equalizer board includes:

at least one potentiometer connected thereto for adjusting the electrode channel gain on at least one electrode channel of said ICS.

29. The apparatus of claim 27 wherein said equalizer board includes:

at least one potentiometer connected thereto for adjusting an input dynamic range of the ICS, said input dynamic range defining a range of stimulation currents that may be generated at levels between the adjusted threshold stimulation level and the adjusted comfortable stimulation level.

30. The apparatus of claim 27 wherein said equalizer board includes:

at least one potentiometer connected thereto for adjusting the electrode channel gain on at least one electrode channel of said ICS; and at least another potentiometer connected thereto for adjusting an input dynamic range of the ICS, said input dynamic range defining a range of stimulation currents that may be generated at levels between the adjusted threshold stimulation level and the adjusted comfortable stimulation level.

31. An apparatus for fitting a patient with an implantable cochlear stimulator (ICS), the ICS including means for generating stimulation currents and at least one electrode channel having an electrode channel gain associated therewith through which stimulation currents may be applied to the patient, the fitting apparatus comprising:

a programmer unit comprising:

a clinician's programmer connected to the programmer unit including means for coupling the programmer unit with the ICS, whereby data may be transferred between the programmer unit and the ICS, the clinician's programmer including:

a first serial interface coupled to the programmer unit, a second serial interface including means for interfacing the clinician's programmer to the implantable cochlear stimulator, and data protocol converter means for converting a first data protocol used by the first serial interface to a second data protocol used by the second serial interface;

storage means for storing data within the programmer unit;

means for prompting entry of data associated with an objective measurement into the storage means of the programmer unit;

means for determining an estimated threshold stimulation current and an estimated comfortable stimulation current as a function of the objective measurement data, the estimated threshold stimulation current defining a lower limit for stimulation current applied to the patient through the at least one electrode channel of the ICS, and the estimated comfortable stimulation current defining an upper limit for the stimulation current applied to the patient; and means for adjusting the estimated threshold stimulation current and the estimated comfortable stimulation current in order to maintain the stimulation currents applied through the at least one electrode channel within a range of stimulation currents that are comfortably perceived by the patient.

32. An apparatus for fitting a patient with an implantable cochlear stimulator (ICS), the ICS including means for generating stimulation currents and at least one electrode channel having an electrode channel gain associated therewith through which stimulation currents may be applied to the patient, the fitting apparatus comprising:

a programmer unit comprising:

a clinician's programmer connected to the programmer unit including means for coupling the programmer unit with the ICS, whereby data may be transferred between the programmer unit and the ICS, the clinician's programmer including:

a first serial interface coupled to the programmer unit, a second serial interface including means for interfacing the clinician's programmer to the implantable cochlear stimulator, and data protocol converter means for converting a first data protocol used by the first serial interface to a second data protocol used by the second serial interface, means for generating a speech signal;

means for determining a threshold stimulation current and a comfortable stimulation current that may be applied to the patient through the at least one electrode channel of the ICS;

means for causing the implantable cochlear stimulator to stimulate the patient with a stimulation current derived from the speech signal, said stimulation current being greater than the threshold stimulation current and less than the comfortable stimulation current, whereby the threshold stimulation current defines a lower limit for the stimulation current and the comfortable stimulation current defines an upper limit for the stimulation current;

means for displaying, in real time, a graphical representation of the stimulation current derived from the speech signal as compared to the threshold stimulation current and the comfortable stimulation current; and means for adjusting the threshold stimulation current and the comfortable stimulation current for the at least one electrode channel of the ICS in order to maintain the stimulation current within a range of stimulation currents that is comfortably perceived by the patient.

* * * * *